(12) United States Patent
Winkley et al.

(10) Patent No.: US 7,026,508 B2
(45) Date of Patent: Apr. 11, 2006

(54) SUCCINATE SALT OF O-DESMETHYL-VENLAFAXINE

(75) Inventors: Michael W. Winkley, Campbell Hall, NY (US); Karen W. Sutherland, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/985,292

(22) Filed: Nov. 10, 2004

(65) Prior Publication Data

US 2005/0096479 A1    May 5, 2005

Related U.S. Application Data

(62) Division of application No. 10/654,756, filed on Sep. 4, 2003, now abandoned, which is a division of application No. 10/073,743, filed on Feb. 11, 2002, now Pat. No. 6,673,838.

(60) Provisional application No. 60/297,963, filed on Jun. 13, 2001, provisional application No. 60/268,214, filed on Feb. 12, 2001.

(51) Int. Cl.
    *C07C 55/00*    (2006.01)

(52) U.S. Cl. .................................................... 562/590
(58) Field of Classification Search ............... 562/590; 564/336

See application file for complete search history.

(56) References Cited

U.S. PATENT DOCUMENTS 4,535,186 A    8/1985    Husbands et al.

FOREIGN PATENT DOCUMENTS

| EP | 0 112 669 | 7/1984 |
|----|-----------|--------|
| WO | WO 00/32555 | 6/2000 |
| WO | WO 00/59851 | 10/2000 |
| WO | WO 00/76955 | 12/2000 |

OTHER PUBLICATIONS

Majetich et al, Tetrahedron Letters, Hydride-promoted Demethylation of Methyl Phenyl Ethers, 1994, 35(47), pp. 8727-8730.*

* cited by examiner

*Primary Examiner*—Paul A. Zucker
(74) *Attorney, Agent, or Firm*—Rebecca R. Barrett

(57) ABSTRACT

A novel salt of O-desmethyl venlafaxine is provided, O-desmethylvenlafaxine succinate. Pharmaceutical compositions, dosage forms and methods of use are also provided.

16 Claims, 12 Drawing Sheets

SUCCINATE SALT OF O-DESMETHYL-VENLAFAXINE

This application is a divisional of application Ser. No. 10/654,756, filed on Sep. 4, 2003, now abandoned which is a divisional of application Ser. No. 10/073,743, filed on Feb. 11, 2002, now U.S. Pat. No. 6,673,838, which claims priority from provisional application(s) Ser. Nos. 60/268,214 filed on Feb. 12, 2001 and 60/297,963 filed on Jun. 13, 2001, the entire disclosure of which is hereby incorporated by reference.

FIELD OF THE INVENTION

The present invention provides a novel salt of O-desmethyl-venlafaxine, O-desmethyl-venlafaxine succinate, as well as polymorphs, pharmaceutical compositions, dosage forms, and methods of use with the same.

BACKGROUND OF THE INVENTION

O-desmethyl venlafaxine is a major metabolite of venlafaxine and has been shown to inhibit norepinephrine and serotonin uptake. Klamerus, K. J. et al., "Introduction of the Composite Parameter to the Pharmacokinetics of Venlafaxine and its Active O-Desmethyl Metabolite", *J. Clin. Pharmacol.* 32:716–724 (1992). O-desmethyl-venlafaxine, chemically named 1-[2-(dimethylamino)-1-(4-phenol) ethyl]-cyclohexanol, was exemplified as a fumarate salt in U.S. Pat. No. 4,535,186. However, the fumarate salt of O-desmethyl-venlafaxine has unsuitable physicochemical and permeability characteristics. O-desmethyl-venlafaxine is also exemplified as a free base in International Patent Publication No. WO 00/32555.

Salt formation provides a means of altering the physicochemical and resultant biological characteristics of a drug without modifying its chemical structure. A salt form can have a dramatic influence on the properties of the drug. The selection of a suitable salt is partially dictated by yield, rate and quantity of the crystalline structure. In addition, hygroscopicity, stability, solubility and the process profile of the salt form are important considerations. The identification of a salt form that exhibits a suitable combination of properties can be difficult.

Solubility is one important characteristic of a salt form that can affect its suitability for use as a drug. Where aqueous solubility is low, i.e. less than 10 mg/ml, the dissolution rate at in vivo administration can be rate limiting in the absorption process leading to poor bioavailability. Hygroscopicity is also an important characteristic. Compounds having low hygroscopicity tend to have better stability and easier processing.

SUMMARY OF THE INVENTION

The present invention provides a novel salt of O-desmethyl-venlafaxine, O-desmethyl-venlafaxine succinate (hereinafter referred to as "ODV succinate"). The novel salt of the present invention has properties which are particularly suitable for use as a drug, including improved solubility, permeability, and bioavailability. For example, ODV succinate is well absorbed in the gastrointestinal tract. Furthermore, oral administration of ODV succinate results in a lower incidence of nausea, vomiting, diarrhea, abdominal pain, headache, vaso-vagal malaise, and/or trismus than oral administration of venlafaxine. Additionally, sustained release oral formulations of ODV succinate result in a lower incidence of nausea, vomiting, diarrhea, abdominal pain, headache, vaso-vagal malaise, and/or trismus than oral administration of venlafaxine. Pharmaceutical compositions comprising ODV succinate and pharmaceutically acceptable carriers or excipients are also provided. Preferably, the pharmaceutical compositions comprise an amount of ODV succinate effective to treat the desired indication in an animal, such as a human.

In further embodiments of the present invention are provided methods of treating patients suffering from depression (include, but not limited to, major depressive disorder, bipolar disorder, and dysthymia), anxiety, panic disorder, generalized anxiety disorder, post traumatic stress disorder, premenstrual dysphoric disorder, fibromyalgia, agoraphobia, attention deficit disorder (with and without hyperactivity), obsessive compulsive disorder (including trichotillomania), social anxiety disorder, autism, schizophrenia, obesity, anorexia nervosa, bulimia nervosa, Gilles de la Tourette Syndrome, vasomotor flushing, cocaine and alcohol addiction, sexual dysfunction (including, but not limited to, premature ejaculation), borderline personality disorder, chronic fatigue syndrome, urinary incontinence, pain (including, but not limited to, migraine, chronic back pain, phantom limb pain, central pain, neuopathic pain such as diabetic neuropathy, and postherpetic neuropathy), Shy Drager syndrome, Raynaud's syndrome, Parkinson's disease, and epilepsy comprising providing to a patient an effective amount of ODV succinate. ODV succinate can also be administered to prevent relapse or recurrence of depression, to induce cognitive enhancement, to treat cognitive impairment, and in regimens for cessation of smoking or other tobacco uses. Additionally, ODV succinate can be administered to treat hypothalamic amenorrhea in depressed and non-depressed human females. These methods include administering to a patient in need thereof, an effective amount of ODV succinate or a substantially pure polymorph of ODV succinate, or mixtures thereof.

The present invention also provides four crystalline polymorphic forms of ODV succinate (hereinafter referred to as Forms I, II, III, and IV, respectively) and an amorphous form of ODV succinate. According to a preferred embodiment, the pharmaceutical composition of the present invention comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of Form I, II, III, or IV or the amorphous form of ODV succinate, based upon 100% total weight of ODV succinate in the pharmaceutical composition (or the total weight of crystalline ODV succinate in the pharmaceutical composition).

Another embodiment is a method for preparing the free base of O-desemthyl-venlafaxine by demethylating venlafaxine or a salt thereof with an alkali metal salt of a trialkylborohydride.

DETAILED DESCRIPTION OF THE INVENTION

Definitions

Figure 1:
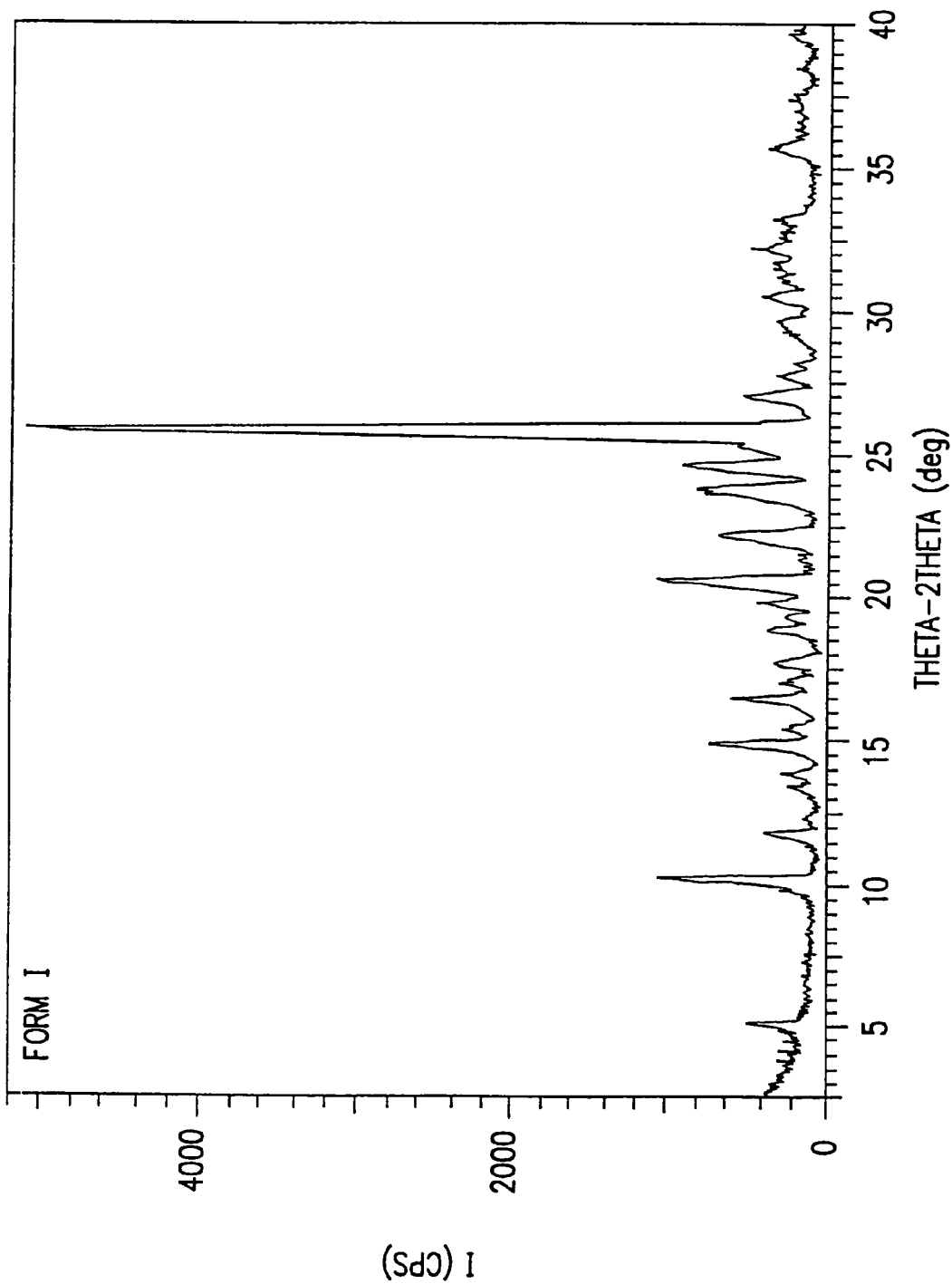
FIG. 1 is an X-ray powder diffractogram (XRPD) of Form I of ODV succinate prepared in Example 7.

The term "about" generally means within 10%, preferably within 5%, and more preferably within 1% of a given value or range. Alternatively, the term "about" means within an acceptable standard error of the mean, when considered by one of ordinary skill in the art.

The term "monohydrate" as used herein refers to a hydrate in which one molecule of water is associated with each molecule of ODV succinate.

The term "hemihydrate" as used herein refers to a hydrate in which one molecule of water is associated with every two molecules of ODV succinate.

The term "treat" as used herein refers to preventing, amelliorating, controlling, or curing the desired symptoms or disorders.

The term "substantially the same" when used to describe X-ray powder deffraction patterns, is meant to include patterns in which peaks are within a standard deviation of ±0.2°2θ.

The present invention relates to a novel salt of O-desmethyl-venlafaxine, O-desmethyl-venlafaxine succinate (hereinafter referred to as "ODV succinate"). ODV succinate provides optimal properties for formulation due to its high solubility, permeability, and bioavailability, and has the structural formula:

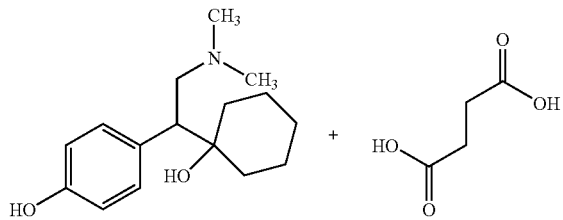

Succinic acid salts of O-desmethyl-venlafaxine exist as enantiomers and this invention includes racemic mixtures as well as stereoisomerically pure forms of the same. The term "ODV succinate" as used herein refers to racemic mixtures and stereoisomerically pure forms of ODV succinate, unless otherwise indicated.

The term "stereoisomerically pure" refers to compounds which are comprised of a greater proportion of the desired isomer than of the optical antipode. A stereoisomerically pure compound is generally made up of at least about 90% of the desired isomer, based upon 100% total weight of ODV succinate.

Succinic acid is a dicarboxylic acid and the invention therefore includes both salts in which the ratio of O-desmethyl-venlafaxine to acid (by mole) is 1:1 (i.e., a monosuccinate) and salts in which the ratio of O-desmethyl-venlafaxine to acid (by mole) is 2:1 (i.e., a bis isuccinate), as well as mixed salts, with for example an alkali metal or ammonium cation. The invention also includes mixtures of ODV succinate and the free base of O-desmethyl-venlafaxine. The crystalline polymorphs (i.e. Forms I, II, III, and IV) and the amorphous form of ODV succinate discussed below are monosuccinate salts, i.e., the molar ratio of O-desmethyl-venlafaxine to acid is 1:1. Salts of the present invention can be crystalline and may exist as more than one polymorph. Each polymorph forms another aspect of the invention. Hydrates as well as anhydrous forms of the salt are also encompassed by the invention. In particular the monohydrate form of O-desmethyl venlafaxine succinate is preferred.

ODV succinate generally has a solubility in water of greater than 30 mg/mL. Preferably, the aqueous solubility of the ODV succinate is at least 25, 30, 32, 35, 40, or 45 mg/mL at 25° C.

Succinic acid salts may be formed by contacting stoichiometric amounts of the acid with O-desmethy-venlafaxine free base. Alternatively, the acid may be used in excess, usually no more than 1.5 equivalents. Preferably the base and/or the acid are in solution, more preferably both are in solution.

The crystalline salt may be prepared by directly crystallizing from a solvent. Improved yield may be obtained by evaporation of some or all of the solvent or by crystallization at elevated temperatures followed by controlled cooling, preferably in stages. Careful control of precipitation temperature and seeding may be used to improve the reproducibility of the production process and the particle size distribution and form of the product.

Form I

Crystalline polymorph Form I of ODV succinate is a monohydrate and is stable at room temperature. Form I is physically stable up to at least about 105° C. and at 5–95% relative humidity. According to differential scanning calorimetry (DSC), Form I has an endotherm at about 131° C. (see FIG. 6). Form I of ODV succinate has an XRPD pattern substantially identical to that shown in FIGS. 1 (ground Form I) and 7 (unground Form I). Peak locations and intensities for the XRPD pattern in FIG. 1 are provided in Table 1 below.

TABLE 1

Characteristic XRPD Peaks (expressed in degrees 2θ ± 0.2° 2θ) and Relative Intensities of Diffraction Lines for Form I of ODV Succinate

| Degrees 2θ ± 0.2° 2θ | I/I₁ |
| --- | --- |
| 10.20 | 17 |
| 14.91 | 12 |

TABLE 1-continued

Characteristic XRPD Peaks (expressed in degrees 2θ ± 0.2° 2θ) and Relative Intensities of Diffraction Lines for Form I of ODV Succinate

| Degrees 2θ ± 0.2° 2θ | I/I$_1$ |
|---|---|
| 20.56 | 18 |
| 22.13 | 11 |
| 23.71 | 13 |
| 24.60 | 14 |
| 25.79 | 100 |

In particular, the peaks (expressed in degrees 2θθ±0.2° 2θ) at 10.20, 14.91, 20.56, 22.13, 23.71, 24.60, and 25.79 are characteristic of Form I.

Form I may be prepared from the free base of O-desmethyl-venlafaxine as follows. The free base of O-desmethyl-venlafaxine and succinic acid are dissolved in aqueous acetone. The resulting solution may optionally be filtered to remove any byproducts, such as those produced during the preparation of the free base of O-desmethyl-venlafaxine. The solution is then slowly cooled (e.g., for 3 hours or longer) to yield Form I of ODV succinate. The crystals of Form I may be recovered by any method known in the art.

Form I can also be prepared by preparing a slurry containing (a) Form I and (b) Form II, Form III, or a mixture thereof with (c) acetone, acetonitrile, a mixture of acetonitrile and water (e.g., a 9:1 mixture), or a mixture of ethanol and toluene (e.g., a 1:1 mixture) at ambient temperature.

Any crystals prepared by the aforementioned methods may be recovered by technique known to those silled in the art, such as, for example, filtration.

Form II

Figure 2:
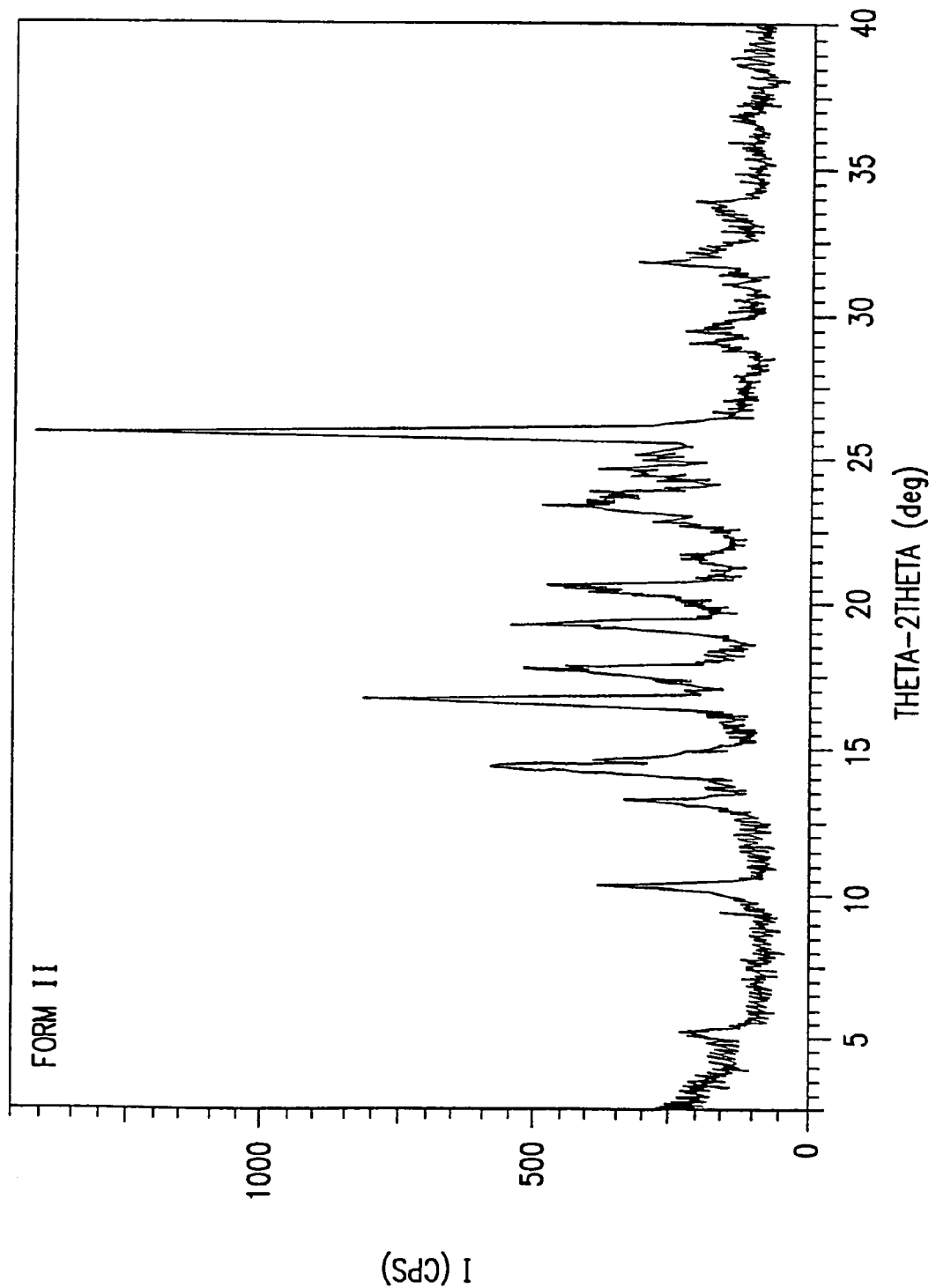
FIG. 2 is an XRPD of Form II of ODV succinate prepared in Example 8.

Crystalline polymorph Form II of ODV succinate is a monohydrate and is more thermally stable than Form III. According to DSC, Form II has an endotherm at about 127° C. (see FIG. 6). Form II of ODV succinate has an XRPD pattern substantially identical to that shown in FIG. 2. Peak locations and intensities for the XRPD pattern in FIG. 2 are provided in Table 2 below.

TABLE 2

Characteristic XRPD Peaks (expressed in degrees 2θ ± 0.2° 2θ) and Relative Intensities of Diffraction Lines for Form II of ODV Succinate

| Degrees 2θ ± 0.2° 2θ | I/I$_1$ |
|---|---|
| 10.25 | 22 |
| 13.18 | 14 |
| 14.04 | 10 |
| 14.35 | 35 |
| 14.66 | 18 |
| 16.68 | 52 |
| 17.67 | 29 |
| 19.24 | 29 |
| 20.38 | 16 |
| 20.56 | 25 |
| 23.41 | 24 |
| 23.78 | 16 |
| 24.57 | 13 |
| 25.13 | 10 |
| 25.80 | 100 |
| 31.78 | 14 |

In particular, the peaks (expressed in degrees 2θ±0.2° 2θ) at 13.18, 14.04, 14.35, 14.66, 16.68, 17.67, 19.24, 25.13, and 31.78 are characteristic of Form II.

Form II can be prepared by rotary evaporation of Form I dissolved in acetone.

Form II can also be prepared by slow cooling of either saturated acetone or 95:5 ethanol:water solutions of Form I of ODV succinate. According to one embodiment, slow cooling is performed as follows. A mixture of the solvent and Form I of ODV succinate is prepared and heated and stirred on a hotplate (preferably set at 60–75° C.). Solvent is added until the ODV succinate is nearly all dissolved. The resulting mixture is optionally filtered (e.g., through a 0.2-µm nylon filter) into a clean vial pre-warmed, preferably on the same hotplate. The heat source is turned off, and the hotplate and vial are allowed to cool to ambient temperature. The vial is then allowed to stand at ambient temperature overnight. If no solids are generated, the vial is placed in a refrigerator for at least one day. Again, if no solids are generated, the vial is placed in a freezer for at least one day. Any solids are removed by vacuum filtration and allowed to air dry. In cases where no solid is obtained, a portion of the solvent is allowed to evaporate, and the procedure is repeated with heating and filtering.

Yet another method for preparing Form II is by precipitating Form I of ODV succinate from a solvent/anti-solvent mixture of ethanol/hexanes. Suitable solvents include those in which ODV succinate has a solubility of greater than 1 mg/mL. Suitable anti-solvents include those in which ODV succinate has low solubility, e.g., a solubility of less than 1 mg/mL. According to one embodiment, the solvent is saturated with ODV succinate. The mixture is heated, if necessary, to dissolve the ODV succinate. The mixture is filtered (e.g., through a 0.2-µm nylon filter) into a vial of cold anti-solvent (e.g., a solvent in which ODV succinate has a solubility of less than 0.1%). The resulting mixture may be placed in a freezer to increase the yield.

Form II can be prepared by slow evaporation of Form I of ODV succinate from water. For example, Form I of ODV succinate may be dissolved in water and then left in a perforated container at ambient temperature to form crystalline polymorph Form II.

Form II can be prepared by fast evaporation of Form I of ODV succinate from acetonitrile or ethanol/hexanes or ethanol/chloroform mother liquors. For example, Form I of ODV succinate may be dissolved in the solvent and then left in an open container at ambient temperature to form crystalline polymorph Form II.

Form II can be prepared by rapid cooling of an aqueous or aqueous/acetone solution of ODV succinate. Rapid cooling can be performed by any method known in the art, such as, for example, by applying a vacuum and/or an ice or ice/water bath.

Form II can also be prepared by subjecting the amorphous form of ODV succinate to 75% or greater relative humidity (e.g., at room temperature).

Any crystals prepared by the aforementioned methods may be recovered by known techniques.

Form III

Figure 3:
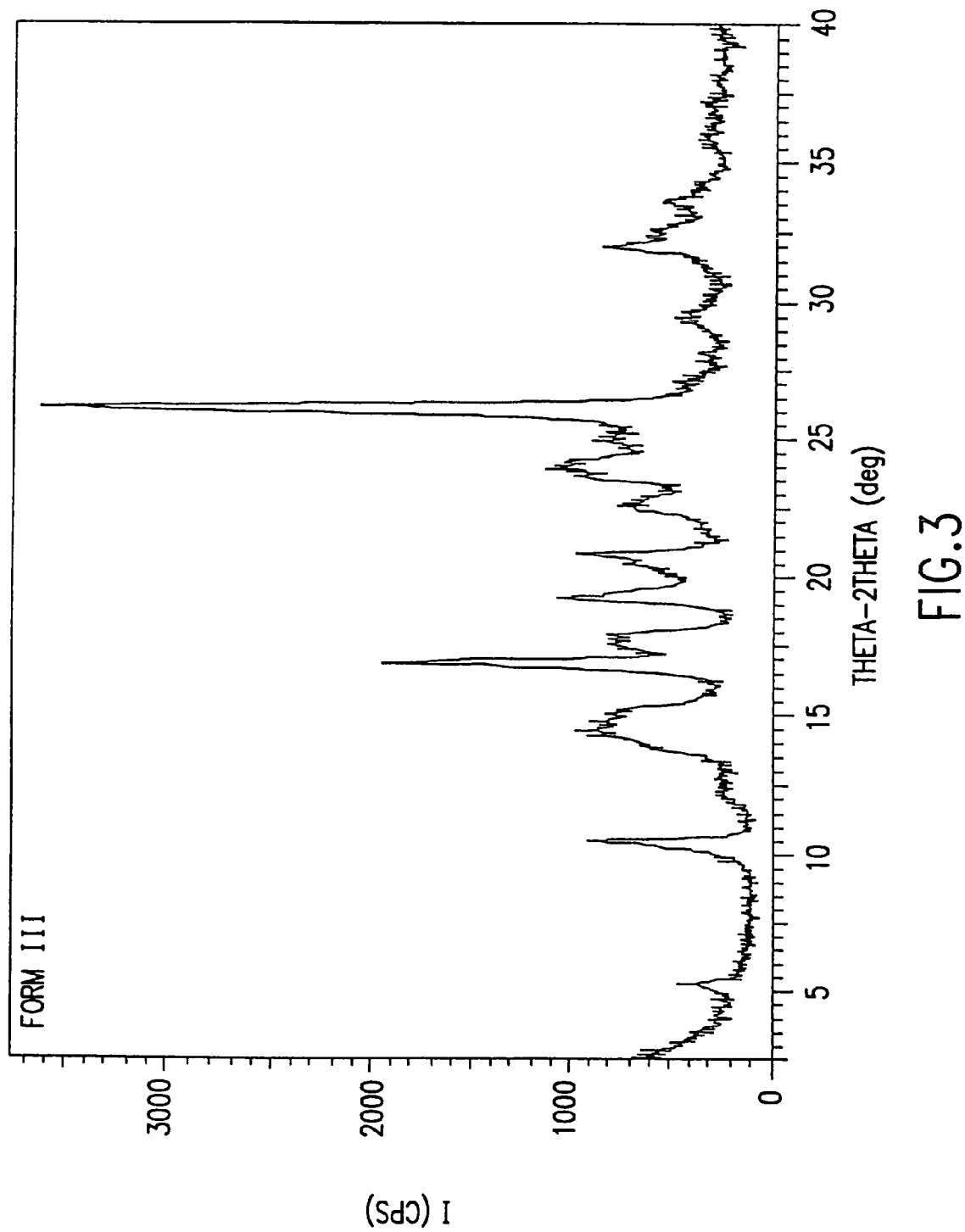
FIG. 3 is an XRPD of Form III of ODV succinate prepared in Example 9.

Crystalline polymorph Form III of ODV succinate is a hydrate. The molar ratio of water to ODV succinate is less than 1 but more than ½ (i.e., Form III of ODV succinate is between a hemihydrate and a monohydrate). Form III of ODV succinate has an XRPD pattern substantially identical to that shown in FIG. 3. Peak locations and intensities for the XRPD pattern in FIG. 3 are provided in Table 3 below.

TABLE 3

Characteristic XRPD Peaks (expressed in degrees 2θ ± 0.2° 2θ) and Relative Intensities of Diffraction Lines for Form III of ODV Succinate

| Degrees 2θ ± 0.2° 2θ | I/I₁ |
|---|---|
| 10.36 | 23 |
| 13.74 | 11 |
| 14.40 | 20 |
| 14.68 | 18 |
| 14.96 | 16 |
| 16.75 | 49 |
| 17.48 | 17 |
| 17.76 | 17 |
| 19.26 | 24 |
| 20.42 | 13 |
| 20.74 | 20 |
| 22.55 | 11 |
| 23.58 | 16 |
| 23.82 | 20 |
| 24.92 | 12 |
| 26.00 | 100 |
| 31.86 | 17 |
| 32.42 | 10 |

In particular, the peaks (expressed in degrees 2θ±0.2° 2θ) at about 13.74, 22.55, and 32.42 are characteristic of Form III.

Form III can be prepared by ball milling or cryo-grinding Form I of ODV succinate. Ball milling is performed by placing a ball in a cylinder with the ODV succinate and then shaking the cylinder. Cryo-grinding is performed by placing the ODV succinate in a cylinder and shaking the cylinder while maintaining the temperature of the cylinder at cryogenic temperatures (e.g., at <−90° C.).

Any crystals prepared by the aforementioned methods may be recovered by any known technique.

Form IV

Figure 4:
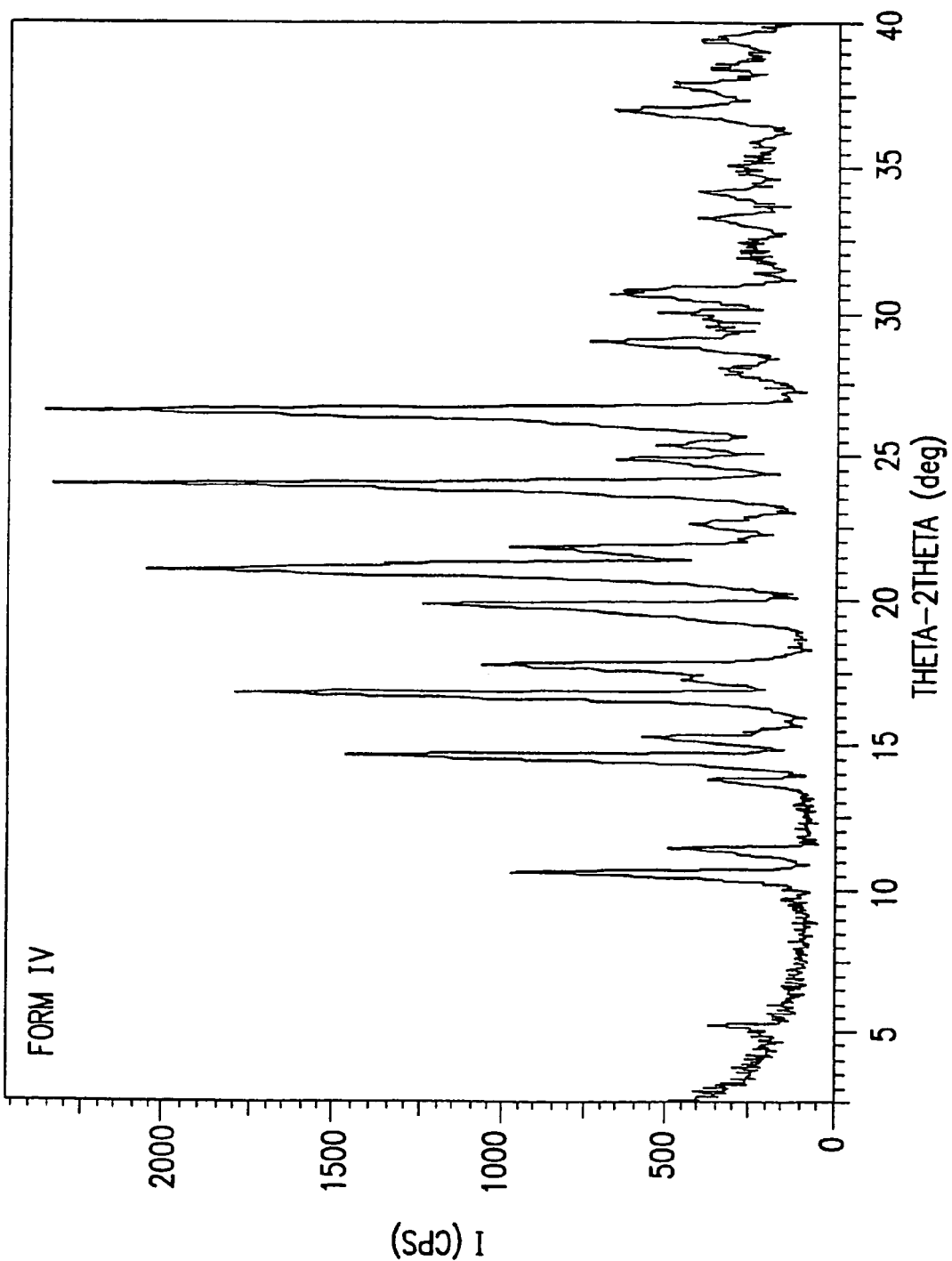
FIG. 4 is an XRPD of Form IV of ODV succinate prepared in Example 10.

Crystalline polymorph Form IV of ODV succinate is anhydrous. According to DSC, Form IV has an endotherm at about 145° C. (see FIG. 6). Form IV of ODV succinate has an XRPD pattern substantially identical to that shown in FIG. 4. Peak locations and intensities for the XRPD pattern in FIG. 4 are provided in Table 4 below.

TABLE 4

Characteristic XRPD Peaks (expressed in degrees 2θ ± 0.2° 2θ) and Relative Intensities of Diffraction Lines for Form IV of ODV Succinate

| Degrees 2θ ± 0.2° 2θ | I/I₁ |
|---|---|
| 10.46 | 36 |
| 11.29 | 15 |
| 13.69 | 10 |
| 14.48 | 60 |
| 15.17 | 18 |
| 16.62 | 74 |
| 17.22 | 14 |
| 17.61 | 42 |
| 19.22 | 10 |
| 19.64 | 48 |
| 20.91 | 83 |
| 21.61 | 33 |
| 22.55 | 12 |
| 23.84 | 89 |
| 24.77 | 21 |
| 25.34 | 15 |
| 25.92 | 21 |
| 26.40 | 100 |
| 28.86 | 24 |
| 29.80 | 12 |
| 30.60 | 21 |
| 33.17 | 10 |
| 36.85 | 21 |
| 37.70 | 12 |

In particular, the peaks (expressed in degrees 2θ±0.2° 2θ) at about 11.29, 17.22, 19.64, 20.91, 21.61, 28.86, 29.80, 30.60, 36.85, and 37.70 are characteristic of Form IV.

Form IV can be prepared by slurrying equal amounts of Form I and Form II in acetonitrile at about 54° C. for several days (e.g., eight days), filtering, and heating the resulting solid for 18 hours at about 120° C. The crystals can be recovered by any method known in the art.

Amorphous Form

Figure 5:
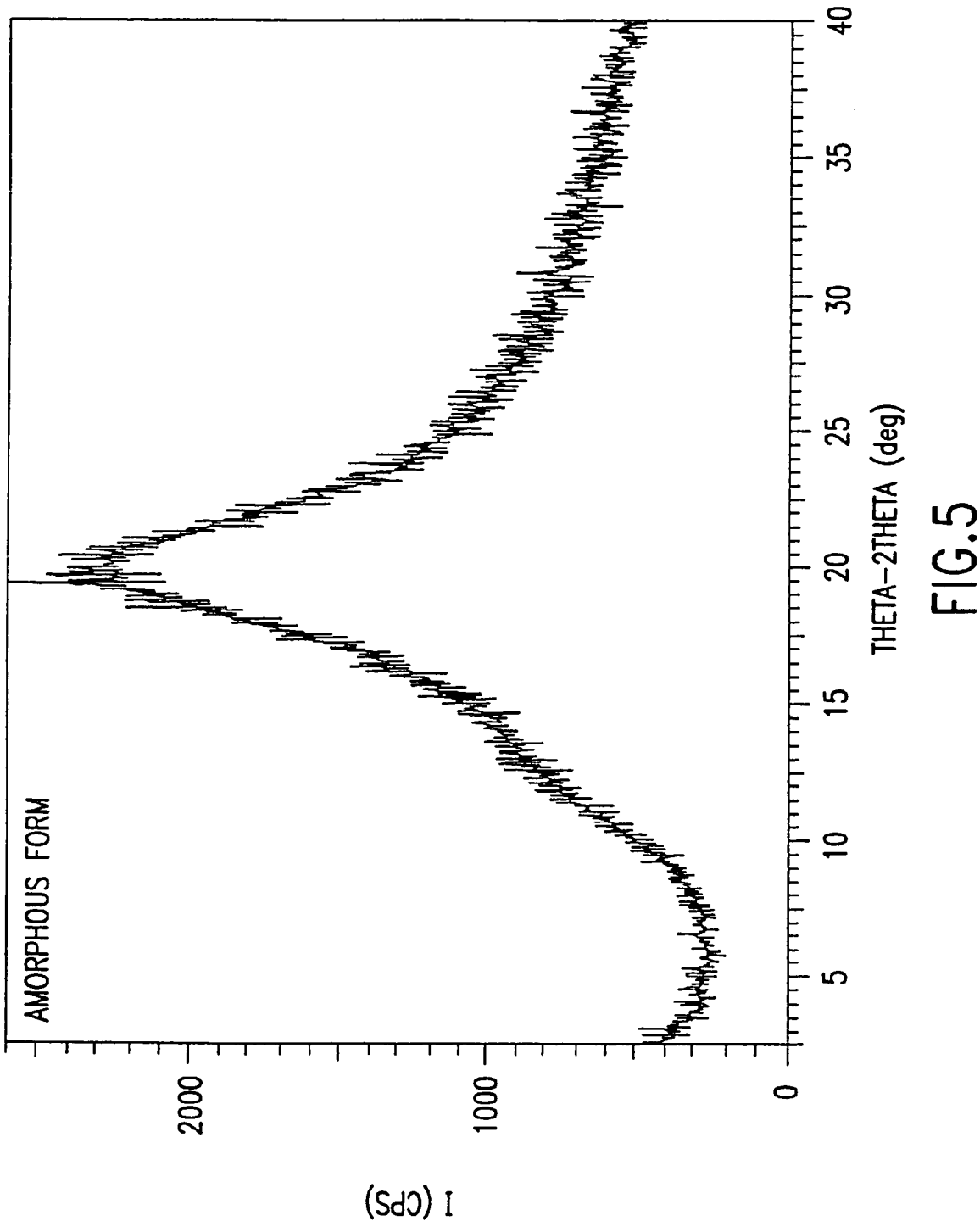
FIG. 5 is an XRPD of the amorphous form of ODV succinate prepared in Example 11.

The amorphous form of ODV succinate has an XRPD pattern substantially identical to that shown in FIG. 5. FIG. 5 shows an amorphous form of ODV succinate. The glass transition ($T_g$) onset for the amorphous form occurs at 18° C. According to DSC, the amorphous form undergoes a major endotherm at about 120° C. (see FIG. 6). Without being bound by any theory, the inventors believe that the amorphous form was converted into a crystalline form before reaching 120° C., since amorphous forms typically do not exhibit endotherms, while crystalline forms do.

The amorphous form can be produced by forming a melt by heating Forms I, II, III, or IV, or a mixture thereof and cooling the melt to form a glass. For example, the amorphous form can be prepared by holding Forms I, II, III, or IV or a mixture thereof at about 150° C. for about 6 to about 18 minutes to form a melt and then cooling the melt to form a glass. The cooling can be done slowly or rapidly (e.g., by crash cooling).

The amorphous form can be converted to Form II by placing the amorphous material in a high relative humidity environment (e.g., greater than about 50 or about 75% relative humidity).

Preparation of ODV Free Base

O-desmethyl-venlafaxine (ODV) free base may be prepared according to the general procedures outlined in U.S. Pat. No. 4,535,186.

Another method of preparing ODV free base is by demethylating a compound of Formula I (venlafaxine) to provide a compound of Formula II as described in Scheme I below.

Scheme I

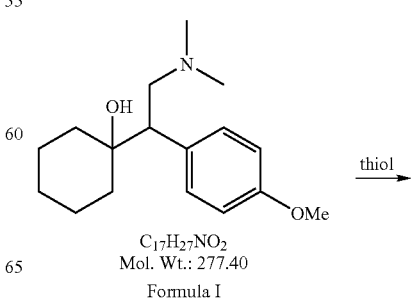

$C_{17}H_{27}NO_2$
Mol. Wt.: 277.40

Formula I

-continued

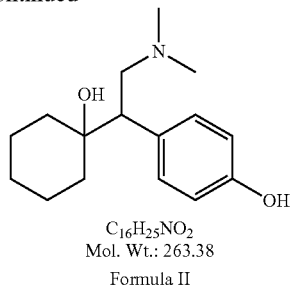

C₁₆H₂₅NO₂
Mol. Wt.: 263.38
Formula II

As described in Scheme I the starting material, venlafaxine (Formula I), is demethylated. Venlafaxine may be prepared in accordance with procedures known in the art, such as those described in U.S. Pat. No. 4,535,186, which is herein incorporated by reference.

Demethylation is performed using a high molecular weight alkane, arene, or arylalkyl thiolate anion, such as straight or branched chain alkane thiolate anions having 8 to 20 carbon atoms, mono or bicyclic arene thiolate anions having 6 to 10 carbon atoms, or mono or bicyclic arylalkyl thiolate anions having 7 to 12 carbon atoms in the presence of a protic or aprotic solvent. Optionally, a base such as an alkoxide comprised of a straight or branched chain alkyl group of from 1 to 6 carbon atoms may be present to generate the thiolate anion.

Preferably the aliphatic thiol has from 10 to 20 carbon atoms and most preferably the aliphatic thiol is dodecanethiol. The aromatic thiol is preferably benzenethiol. The arylalkyl thiolate anion is preferably toluenethiol or naphthylmethanethiol.

When present, the alkoxide is preferably a lower alkoxide (methoxide, ethoxide and the like) such as sodium methoxide (sodium methylate, sodium methanolate).

The solvent is preferably a hydroxylic or ethereal solvent, and more preferably an alcohol, ethylene glycol or ether of ethylene glycol. Ethers of ethylene glycol include, but are not limited to, ethyleneglycol monoethylether, triethyleneglycoldimethylether and polyethylene glycol. Preferably, the solvent is an inert, polar, high boiling point ether of ethylene glycol such as polyethylene glycol and most preferably PEG 400 (polyethylene glycol having a molecular weight range of from about 380–420).

The reaction is performed at a temperature of from about 150° C. to about 220° C., more preferably from about 170° C. to about 220° C., and most preferably from about 180° C. to about 200° C. The reaction is generally allowed to progress until, ideally, not more than 1% venlafaxine remains. In some aspects of the invention the reaction is complete in from about 2 hours to about 5 hours and more preferably in from about 2 to about 3.5 hours.

In preferred embodiments of this method, venlafaxine base is dissolved in polyethylene glycol 400 containing dodecanethiol and sodium methylate as a solution in methanol as the temperature is increased to from about 180° C. to about 200° C., with stirring for about 2 to about 3.5 hours.

Thereafter the reaction mixture is cooled to between about 65° C. and about. 75° C. and an alcohol may be added as a diluent before neutralization to the isoelectric point (about pH 9.5 to about pH 10.0) with an appropriate neutralization agent such as hydrochloric acid. The alcoholic medium may also aid in the crystallization of the product as neutralization is initiated.

Preferably the alcohol comprises a straight or branched chain alkyl group of 1 to 6 carbon atoms, such as methanol, ethanol, isopropanol, butanol, and the like, and mixtures thereof. In some preferred embodiments of this method, the alcohol is isopropanol.

Yields of this method are greater than about 75% and generally from about 85% to greater than 90%.

Yet another method of preparing ODV free base is by demethylating venlafaxine or a salt thereof (e.g., a non-reducible salt of venlafaxine, such as the hydrochloride salt) with an alkali metal salt of a trialkylborohydride. The alkyl groups in trialkylorohydride can independently be $C_1$–$C_6$ alkyl and preferably are independently $C_1$–$C_4$ alkyl. The alkyl substituents on the trialkylborohydride can be the same or different. Suitable alkali metals include, but are not limited to, lithium, sodium, and potassium. Suitable trialkylborohydrides include, but are not limited to, selectride (tri-sec-butylborohydride) or triethylborohydride. Non-limiting examples of suitable salts include L-selectride, K-selectride, lithium triethylborohydride, and potassium triethylborohydride. Preferred salts include, but are not limited to, L-selectride and lithium triethylborohydride. A more preferred salt is L-selectride.

Generally, the demethylation process is performed in one or more of the following solvents: 1,2-dimethoxyethane, tetrahydrofuran (THF), 1,2-dethoxyethane and diglyme (bis (2-methoxyethyl)ether). The reaction is typically performed at or less than the boiling point of the solvent. Preferably, the reaction is performed at a temperature of from about 60 to about 140° C., more preferably from about 80 to about 100° C., and even more preferably from about 85 to about 95° C. The reaction is generally performed until the majority of venlafaxine has been demethylated and preferably until at least 80, 90, 95, or 99% of the venlafaxine has been demethylated. Broadly, the reaction is performed for from about 8 to about 48 hours. According to one embodiment, the reaction is performed for from about 12 to about 36 hours and preferably for about 24 hours.

The reaction results in an alkali metal salt of O-desmethyl-venlafaxine. The alkali metal salt can be converted to its free base by methods known in the art, such as neutralization with acid (e.g., to the isoelectric point).

This process for demethylating venlafaxine does not change the optical activity of the venlafaxine starting material. In other words, if the starting material is a racemic mixture of venlafaxine, the product of this demethylation process will also be a racemic mixture. If the starting material is an optically pure enantiomer, the product of this demethylation process will also be the same optically pure enantiomer.

Figure 14:
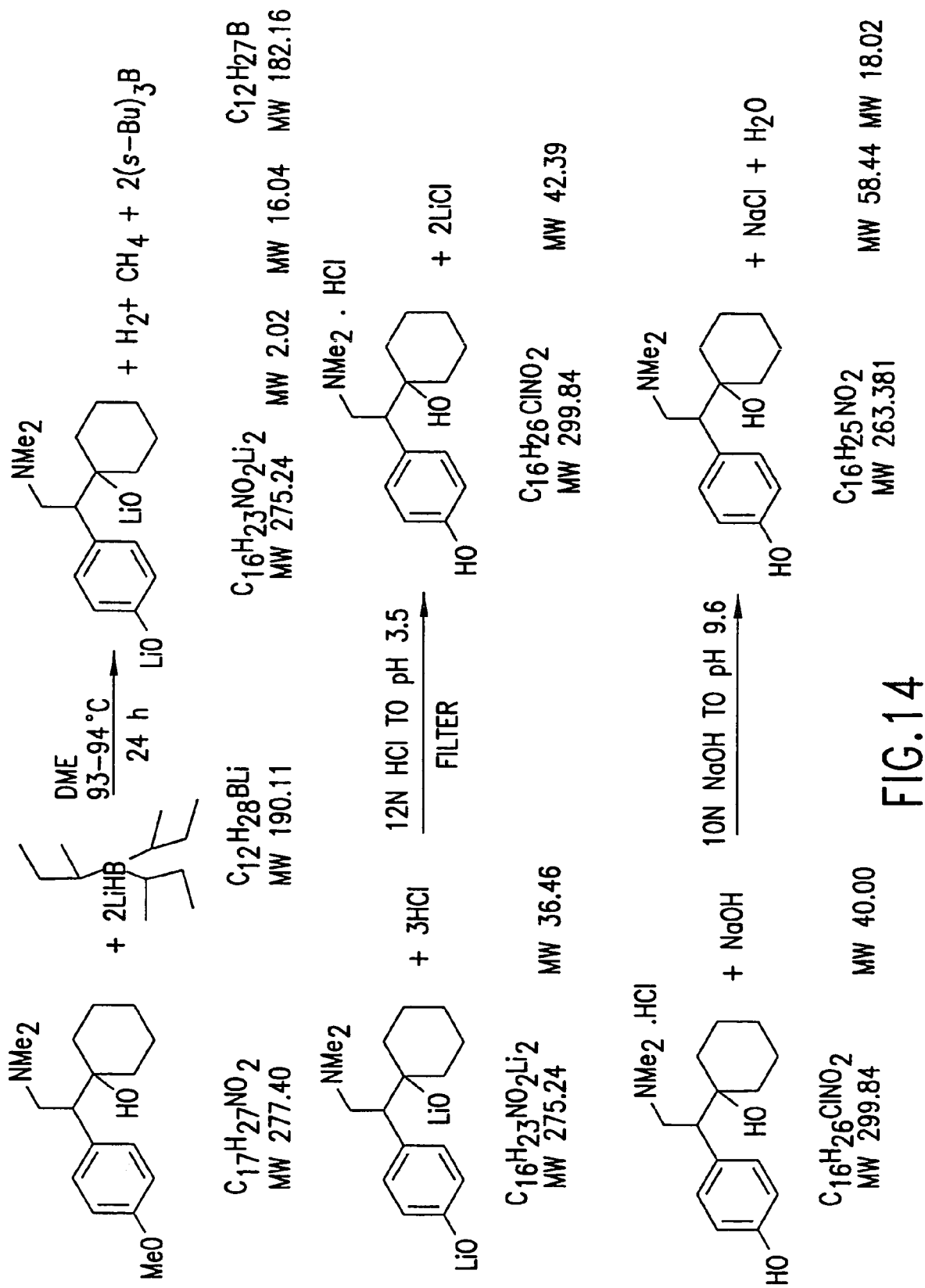
FIG. 14 is a reaction scheme for preparing the free base of O-desmethyl-venlafaxine from venlafaxine with L-selectride.

An example of this reaction scheme for producing O-desmethyl-venlafaxine free base is shown in FIG. 14.

This process for demethylating venlafaxine can produce the free base of ODV in substantially pure form (e.g., with <0.5, 0.4, 0.3, 0.2, 0.1, 0.09, 0.08, 0.07, 0.06, or 0.05% of impurities (w/w) (excluding inorganics) as measured by HPLC).

Demethylation with a trialkylaborohydride produces various hazardous boron containing byproducts. For example, use of L-selectride results in the formation of tris(1-methylpropyl)borane and tris(1-methylpropyl)boroxin as byproducts. These byproducts may be deactivated (or stabilized) by oxidation and, optionally, hydrolysis (of intermediate borate esters). Oxidation may be performed by reacting the boron containing byproducts with an oxidizing agent, such as hydrogen peroxide, perborates (e.g., sodium perborate), or a mixture thereof. A preferred oxidizing agent is an alkaline perborate solution (e.g., an aqueous solution containing sodium hydroxide and sodium perborate tetrahydrate). Preferably, the boron containing byproducts are added to the oxidizing agent or a solution comprising the oxidizing agent.

As described in Reviews in Contemporary Pharmacology, Volume 9(5) page 293–302 (1998), incorporated by reference in its entirety, O-desmethyl-venlafaxine has the following pharmacological profile shown in Table 5 below.

TABLE 5

|  | O-desmethylvenlafaxine |
|---|---|
| Effect (in vivo) | |
| Reversal of Reserpine-Induce Hypothermia (minimum effect; mg/kg i.p.) | 3 |
| Effect (in vitro) | |
| Inhibition of amine reuptake ($IC_{50}$; uM) | |
| Norepinephrine | 1.16 |
| Serotonin | 0.18 |
| Dopamine | 13.4 |
| Affinity for Various Neuroreceptors (% inhibition at 1 uM) | |
| D2 | 6 |
| Cholinergic | 7 |
| Adrenergic α | 0 |
| Histamine H1 | 0 |
| Opiate | 7 |

Thus, compounds, compositions and methods of the present invention can be used to treat or prevent central nervous system disorders including, but not limited to depression (including but not limited to major depressive disorder, bipolar disorder and dysthymia), fibromyalgia, anxiety, panic disorder, agorophobia, post traumatic stress disorder, premenstrual dysphoric disorder (also known as premenstrual syndrome), attention deficit disorder (with and without hyperactivity), obsessive compulsive disorder (including trichotillomania), social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, (including premature ejaculation), borderline personality disorder, chronic fatigue syndrome, incontinence (including fecal incontinence, overflow incontinence, passive incontinence, reflex incontinence, stress urinary incontinence, urge incontinence, urinary exertional incontinence and urinary incontinence), pain (including but not limited to migraine, chronic back pain, phantom limb pain, central pain, neuropathic pain such as diabetic neuropathy, and postherpetic neuropathy), Shy Drager syndrome, Raynaud's syndrome, Parkinson's Disease, epilepsy, and others. Compounds and compositions of the present invention can also be used for preventing relapse or recurrence of depression; to treat cognitive impairment; for the inducement of cognitive enhancement in patient suffering from senile dementia, Alzheimer's disease, memory loss, amnesia and amnesia syndrome; and in regimens for cessation of smoking or other tobacco uses. Additionally, compounds and compositions of the present invention can be used for treating hypothalamic amenorrhea in depressed and non-depressed human females.

In some preferred embodiments of the invention, O-desmethyl-venlafaxine succinate is useful for the treatment of depression, anxiety, panic disorder, generalized anxiety disorder, post traumatic stress and premenstrual dysphoric disorder.

This invention provides methods of treating, preventing, inhibiting or alleviating each of the maladies listed above in a mammal, preferably in a human, the methods comprising administering an effective amount of a compound of the invention to a mammal in need thereof. An effective amount is an amount sufficient to prevent, inhibit, or alleviate one or more symptoms of the aforementioned conditions.

The dosage amount useful to treat, prevent, inhibit or alleviate each of the aforementioned conditions will vary with the severity of the condition to be treated and the route of administration. The dose, and dose frequency will also vary according to age, body weight, response and past medical history of the individual human patient. In generally the recommended daily dose range for the conditions described herein lie within the range of 10 mg to about 1000 mg O-desmethylvenlafaxine per day and more preferably within the range of about 15 mg to about 350 mg/day and still more preferably from about 15 mg to about 140 mg/day. In other embodiments of the invention the dosage will range from about 30 mg to about 90 mg/day. Dosage is described in terms of the free base and is adjusted accordingly for the succinate salt. In managing the patient, is generally preferred that the therapy be initiated at a lower dose and increased if necessary. Dosages for non-human patients can be adjusted accordingly by one skilled in the art.

Another embodiment of the invention is a method of lowering the incidence of nauseau, vomiting, diarrhea, abdominal pain, headache, vaso-vagal malaise, and/or trismus resulting from the oral administration of venlafaxine, O-desmethylvenlafaxine, or a salt of O-desmethylvenlafaxine other than O-desmethylvenlafaxine succinate to a patient. The method includes orally administering to a patient in need thereof a therapeutically effective amount of O-desmethyl-venlafaxine succinate.

Yet another embodiment of the invention is a method of lowering the incidence of nauseauu, vomiting, diarrhea, abdominal pain, headache, vaso-vagal malaise, and/or trismus resulting from the oral administration of O-desmethyl-venlafaxine succinate to a patient. The method includes orally administering to a patient in need thereof a therapeutically effective amount of a sustained release oral dosage form comprising O-desmethyl-venlafaxine succinate having a peak blood plasma level of less than about 225 ng/ml.

O-desmethylvenlafaxine succinate may also be provided in combination with venlafaxine. The dosage of venlafaxine is preferably about 75 mg to about 350 mg/day and more preferably about 75 mg to about 225 mg/day. Still more preferably the dosage of venlafaxine is about 75 mg to about 150 mg/day. The ratio of O-desmethylvenlafaxine to venlafaxine will vary from patient to patient depending upon a patient's response rate, but generally will be at least 6:1 O-desmethylvenlafaxine to venlafaxine.

Any suitable route of administration can be employed for providing the patient with an effective amount of O-desmethylvenlafaxine succinate. For example, oral, mucosal (e.g. nasal, sublingual, buccal, rectal or vaginal), parental (e.g. intravenous or intramuscular), transdermal, and subcutaneous routes can be employed. Preferred routes of administration include oral, transdermal and mucosal.

O-desmethyl venlafaxine succinate can be combined with a pharmaceutical carrier or excipient (e.g., pharmaceutically acceptable carriers and excipients) according to conventional pharmaceutical compounding technique to form a pharmaceutical composition or dosage form. Suitable pharmaceutically acceptable carriers and excipients include, but are not limited to, those described in Remington's, *The Science and Practice of Pharmacy*, (Gennaro, A. R., ed., 19th edition, 1995, Mack Pub. Co.) which is herein incorporated by reference. The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human). For oral liquid pharmaceutical compositions, pharmaceutical carriers and excipients can include, but are not limited to water, glycols, oils, alcohols, flavoring agents, preservatives, coloring agents, and the like. Oral solid pharmaceutical compositions may include, but are not limited to starches, sugars, microcrystalline cellulose, diluents, granulating agents, lubricants, binders and disintegrating agents. The pharmaceutical composition and dosage form may also include venlafaxine or a salt thereof as discussed above.

According to one embodiment, the majority of ODV succinate particles in a pharmaceutical composition or dosage form of the present invention have a particle size between 45 and 400 microns. Preferably, more than 60 or 65% of the particles have a particle size between 45 and 400 microns.

Dosage forms include, but are not limited to tablets, capsules, troches, lozenges, dispersions, suspensions, suppositories, ointments, cataplasms, pastes, powders, creams, solutions, capsules (including encapsulated spheroids), and patches. The dosage forms may also include immediate release as well as formulations adapted for controlled, sustained, extended, or delayed release. Most preferably tablets and capsules are the dosage form. Tablets and spheroids may be coated by standard aqueous and nonaqueous techniques as required.

Each dosage form generally contains from about 15 to about 350 mg of ODV succinate (as measured by the free base equivalent). More preferably, each dosage form contains from about 30 to about 200 mg of ODV succinate (as measured by the free base equivalent) and even more preferably from about 75 to about 150 mg of ODV succinate (as measured by the free base equivalent).

According to one preferred embodiment, the pharmaceutical composition is an extended release formulation, such as that described in U.S. Pat. No. 6,274,171, which is herein incorporated by reference. For example, an extended release formulation may comprise spheroids comprised of ODV succinate, microcrystalline cellulose, and, optionally, hydroxypropylmethylcellulose. The spheroids are preferably coated with a film coating composition comprised of ethyl cellulose and hydroxypropylmethylcellulose.

According to another preferred embodiment, the pharmaceutical composition is a sustained release formulation (e.g., in the form of a tablet). The sustained release formulation may comprise ODV succinate, a rate controlling polymer material (i.e., a material which controls the rate at which the ODV succinate is released), and, optionally, other adjuvants. Suitable rate controlling polymer materials include, but are not limited to, hydroxyalkyl cellulose, such as hydroxypropyl cellulose and hydroxypropyl methyl cellulose (HPMC); poly(ethylene) oxide; alkyl cellulose, such as ethyl cellulose and methyl cellulose; carboxymethyl cellulose; hydrophilic cellulose derivatives; and polyethylene glycol. The sustained release formulation comprises from about 30 w/w to about 50% w/w of ODV succinate and from about 25 w/w to about 70% w/w of a rate controlling polymer material. Optionally, the sustained release formulation may further comprise from about 0.5 w/w to about 10% w/w and preferably from about 2 w/w to about 10% of microcrystalline cellulose. A preferred sustained release formulation comprises from about 32 w/w to about 44% w/w of ODV succinate and from about 45 w/w to about 66% w/w of hydroxyprpopyl methylcellulose. Typically, the sustained release formulation provides sustained therapeutically effective plasma levels over at least a 16 or 20 hour period. The peak serum levels during the 16 or 20 hour period are generally up to 150 ng/ml. The sustained release formulation also shows a reduced level of nausea, vomiting, diarrhea, abdominal pain, headache, vaso-vagal malaise, and/or trismus The following examples are illustrative but are not meant to be limiting of the present invention.

EXAMPLE 1

Preparation of Form I of ODV Succinate

Acetone (2111 mL), water (667 mL) and O-desmethylvenlafaxine (250.0 g, 0.949 mol) were mixed to form a thick white suspension which was stirred at 23° C. for 0.5 hour. Succinic acid (115.5 g, 0.978 mol) was added with acetone (236 mL) and water (75 mL). The suspension was heated to 58° C. and stirred at this temperature for 30 minutes. The reaction mixture was filtered and allowed to cool to 30–34° C. The suspension was stirred at 30–31° C. for 3 hours then cooled to 0–5° C. and stirred at this temperature for a further hour. The solids were isolated by filtration and the wet cake dried at 30° C. for 12 hours (50 mm Hg) then 40° C. for 24 hours (50 mm Hg) to afford O-des-methyl-Venlafaxine succinate monohydrate as white crystals (325.5 g, 85.7%).

mp: 122.3 C and 139.6C $^1$H NMR (300 MHz, DMSO-d$_6$) 10–9 (bs, 2H), 7.00 (d, J=8.2 Hz, 2H), 6.65 (d, J=8.2 Hz, 2H), 3.4–3.2 (bs, 1H), 3.12 (dd, J=7.0, 12.2 Hz, 1H), 2.74 (t, J=8.7 Hz, 1H), 2.7–2.58 (m, 1H), 2.50 (s, 3H), 2.36 (s, 3H), 2.28 (s, 4H), 1.50–1.25 (m, 6H), 1.20–0.80 (4H). 99.40% Purity (by HPLC).

Figure 7:
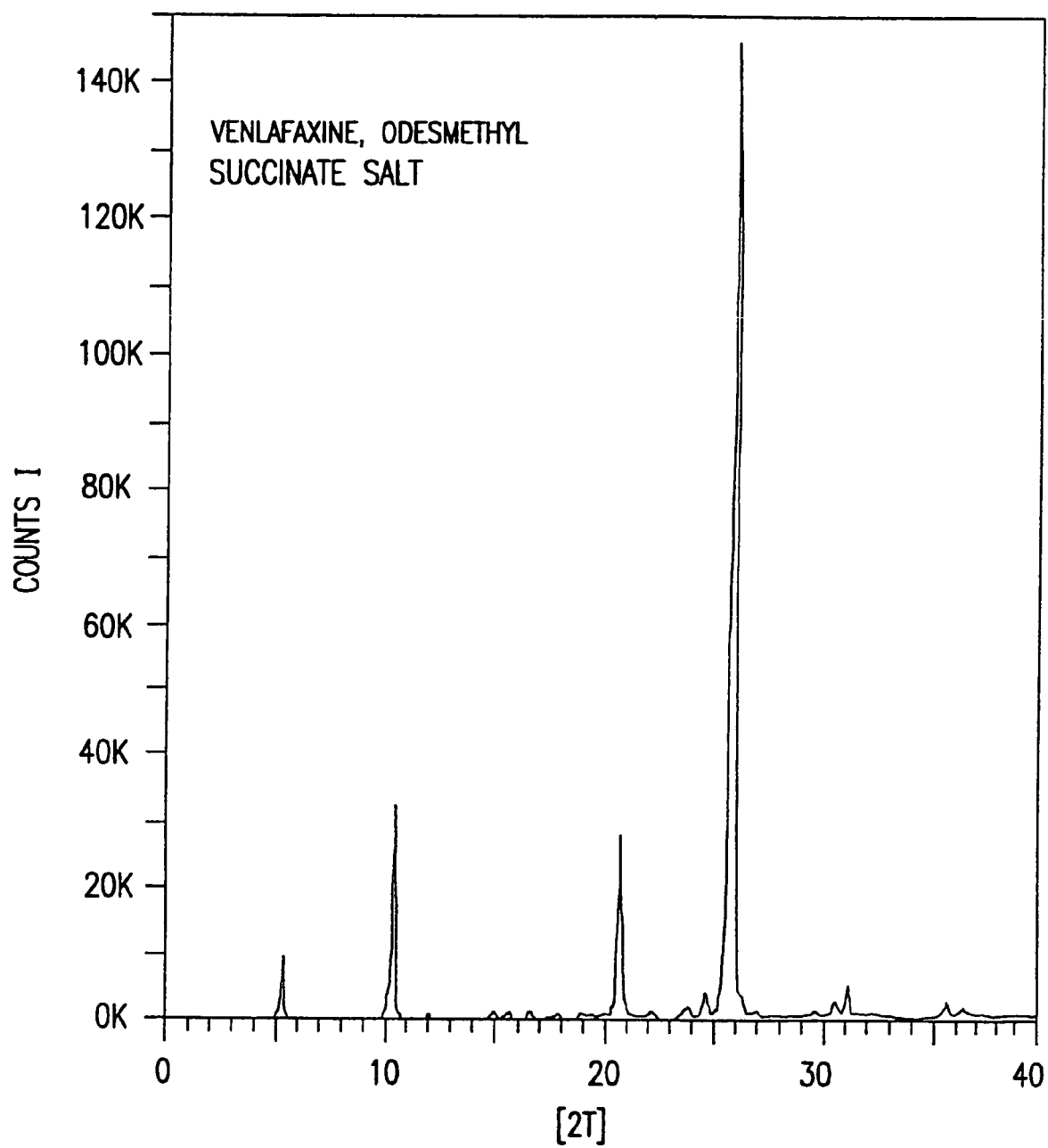
FIG. 7 is an XRPD of Form I of the ODV succinate prepared in Example 1.

An XRPD pattern for the (unground) crystals prepared is shown in FIG. 7. Characteristic XRPD peaks are shown in Table 6 below.

TABLE 6

| X-ray powder diffractogram (CuK2α) | |
|---|---|
| Angle (° 2θ) | Relative Intensity |
| 5.285 | 30.6 |
| 10.435 | 54.6 |
| 20.680 | 10.4 |
| 20.850 | 23.2 |
| 25.660 | 6.6 |
| 25.955 | 55.5 |
| 26.125 | 100.0 |

The crystals of Form I examined in FIG. 7 were not ground, while those in FIG. 1 were ground before being examined. Without being bound by any theory, the inventors theorize that the XRPD for the unground crystals differed from that of the ground crystals due to the preferred orientation of the unground crystals.

Bulk Density: 0.369 gms/mL

Solubility in water: 32.2 mg/ml at 25° C.

The aqueous solubility (reported above) of Form I of ODV succinate was determined according to the following procedure.

Materials

Spectrophotometer—Capable of isolating a bandwidth of 2 nm or less at the wavelength of maximum absorbance, and of measuring absorbances in the 0.0 to 1.0 range with a precision of 0.01. A Cary Model 219 spectrophotometer or equivalent is suitable.

Cells—Silica, 1 cm.

Filters—0.45 micron Nylon filters which are chemical resistant or equivalent

Bottles—Glass screw top bottles having a 15 mL or greater capacity.

Shaker—A lateral shaker, wrist shaker, or a vibrator which will not generate heat is suitable.

Sample Preparation

A. For Non UV Absorbing Solvents

1. To a bottle weigh an amount of sample equivalent to approximately 1½ times the solubility.
2. Pipet 10.0 mL of water into the bottle and secure cap tightly.
3. Agitate the bottles at ambient room temperature for at least 16 hours.
4. Obtain a clear filtrate layer by either centrifugation ot filtration being careful to avoid evaporation.
5. Quantitatively transfer the solution to a volumetric flask and dilute to volume with water.
6. Blank the instrument for water.
7. Make quantitative dilutions to arrive at a suitable concentration for measurement.

B. For UV Absorbing Solvents

1. To a bottle, weigh an amount of sample equivalent to approximately 1½ times the solubility.
2. Pipet 10.0 mL of water into the bottle and secure a cap tightly.
3. Agitate the bottles at ambient room temperature for at least 16 hours.
4. Obtain a clear filtrate layer by either centrifugation or filtration being careful to avoid evaporation.
5. Evaporate an accurate amount of solvent on a steam bath and redissolve the residue, in the solvent used to prepare the standard. Quantitatively transfer to a volumetric flask with the same solvent used in preparing the standard solution.
6. Make dilutions as necessary to obtain a concentration suitable for quantitative measurement.

Procedure

1. Obtain the spectra of the sample and standard preparations between 350 and 200 nm, using water as the blank. The wavelength range may be varied depending upon the UV cut off of water.
2. Calculate the aqueous solubility with the following equation:

$$mg/mL = \frac{(As)(Ds)(Wg - Wt)(S)}{(Ar)(Dr)(V)}$$

where

As=absorbance of the sample preparation

Ds-=dilution factor of the sample preparation, mL

Wg=gross weight of the reference standard and container, mg

Wt=tare weight, mg

S=strength of the reference standard, decimal

Ar=absorbance of the reference standard preparation

Dr=dilution factor of the reference standard preparation, mL

V=amount of solvent evaporated, mL

EXAMPLE 2

Hard Gelatin Capsule Dosage Form

| Ingredient | mg/capsule | % w/w |
|---|---|---|
| ODV succinate | 116.7 (75 as free base) | 39.5 |
| Lactose Fast Flow | 177.3 | 60.0 |
| Magnesium Stearate | 1.5 | 0.5 |
| Total | 295.5 | 100.0 |

The active ingredient is sieved and blended with the listed excipients. Suitably sized hard gelatin capsules are filled using suitable machinery and methods well known in the art. Other doses may be prepared by altering the fill weight and, if necessary, by changing the capsule size to suit.

EXAMPLE 3

Preparation of O-desmethyl-venlafaxine Free Base

Dodecanethiol (122 g), venlafaxine (111 g), and a methanolic solution of sodium methanolate (30%, 90 g) and PEG 400 are heated to 190° C. The methanol is distilled off and the solution is stirred for 2 hours at 190° C. Then the temperature is lowered, 2-propanol (450 g) is added and the pH is adjusted to 9.5 with aqueous HCl. The precipitate is collected by suction filtration, and the cake is washed with 2-propanol, toluene, 2-propanol and water. The wet O-desmethylvenlafaxine is dried in vacuo.

Yield: 87 g. $^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H) 2.15 (s, 6H, 2×Me), 1.7–0.8 (m, 10H, c-hex).

EXAMPLE 4

Preparation of O-desmethyl-venlafaxine Free Base

Venlafaxine (5.6 g) and benzenethiol sodium salt (6.9 g) are charged to PEG 400 (25 g). The reaction mixture is heated to 160° C. for 5 hours. Then the temperature is lowered and water is added (60 g). The pH is adjusted to 3.5 with $H_3PO_4$. The organic by-products are removed by extraction with heptanes (25 g). The pH of the aqueous layer is then adjusted to 9.5 with aqueous ammonia. The precipitate is collected by suction filtration, re-slurried in water (100 g), isolated by suction filtration and dried in vacuo.

Yield 1 g. $^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE 5

Preparation of O-desmethyl-venlafaxine Free Base

Dodecanethiol (69 g), venlafaxine (55 g), and an ethanolic solution of sodium ethanolate (21%, 82 g) are charged to a pressure vessel. The temperature is raised to 150° C. and the reaction mixture is stirred for 2 days. Then the temperature is lowered and the solution is filtered. The pH of the filtrate is adjusted to 9.5 with aqueous hydrogen chloride. The crystals are collected by suction filtration. The cake is washed with ethanol and dried in vacuo.

Yield: 42 g $^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE 6

Preparation of O-desmethyl-venlafaxine Free Base

A 12 L multi-necked flask, equipped with a mechanical stirrer, a thermometer, a 1 L pressure equalizing dropping funnel, and a Claisen distillation head equipped with a downward condenser attached to a 5 L receiver with a vacuum take-off, was placed in a heating mantle. The system was purged with nitrogen and a nitrogen atmosphere was maintained. The distillation flask was charged with 4.00 L (4.00 mol, 5.55 molar excess) of 1 M L-selectride. The dropping funnel was charged with a solution of 200.00 g (0.720 mol) of venlafaxine base in 0.6936 kg (800 mL) of anhydrous 1,2-dimethoxyethane while maintaining the nitrogen atmosphere. The solution of venlafaxine base was added to the stirred L-selectride solution over a period of 15 minutes using rinses of 1,2-dimethoxyethane (2×400 mL, 2×0.3468 kg). Hydrogen was vented and bubbled through a dispersion tube into water. No significant temperature change occurred during the addition.

The dropping funnel was replaced with a similar 4 L funnel charged with 2.4276 kg (2800 mL) of anhydrous 1,2-dimethoxyethane. The system was again purged with nitrogen and a nitrogen atmosphere was maintained. The solution was heated and distilled at atmospheric pressure until the liquid level reached the 4 L mark and the reaction flask temperature was 84–85° C. While distilling, 2.4276 kg (2800 mL) of 1,2-dimethoxyethane was added dropwise at a rate which maintained the liquid level at the 4.00 L level until the temperature in the reaction flask reached 93–94° C. A crystalline precipitate was observed. The distillate was discarded.

The stirred slurry of crystals was cooled to 90° C., the stirrer was stopped, and the dropping funnel and distillation equipment was removed. The flask was then equipped with a reflux condenser fitted with a nitrogen inlet. The system was purged with nitrogen and a nitrogen atmosphere was maintained. The slurry was stirred and heated at reflux under a nitrogen atmosphere for about 19 hours. The initial temperature of the slurry at reflux was 94–96° C. and the final temperature was 97° C. Copious crystallization occurred. The slurry was cooled to room temperature.

12 L of distilled water in a 20 L Duran flask was purged with nitrogen to remove oxygen and carbon dioxide. The purging was repeated as necessary. This water is hereinafter referred to as "nitrogen purged distilled water".

The heating mantle was removed and replaced with an ice/water bath to bring the temperature of the reaction mixture to near room temperature. The flask was equipped with a 1000 mL pressure equalizing dropping funnel. The stirred reaction mixture was cooled with an ice/alcohol bath to obtain a temperature of 15–20° C. While the nitrogen atmosphere was maintained, the reaction mixture was quenched by dropwise addition of 0.296 kg (296 mL) of the nitrogen purged distilled water. The addition was controlled so as to maintain the temperature below 25° C. The temperature rose to 15–24° C. as a result of an exotherm. The mixture was stirred at ambient temperature for about 1 hour. A thick gel-like precipitate, which was formed initially, was converted into a crystalline precipitate during this period. While the reaction mixture was maintained in the nitrogen atmosphere, the flask was equipped with a Claisen distillation head, a downward condenser with a vacuum take-off and a 5 L receiving flask chilled in an ice/water bath. The stirred reaction mixture was distilled under pump vaccum (109–134 mm Hg) down to the 2.80 L mark at a distillation flask temperature of 25–38° C. The distillate was discarded. 3.00 kg (3000 mL) of nitrogen purged distilled water was added.

The stirred mixture was distilled under pump vacuum (113–187 mm Hg) down to 2.80 L at a distillation flask temperature of 35–50° C. to form a biphasic mixture. The distillate (Distillate A) was discarded by the Waste Treatment procedure described below. The warm biphasic mixture (35–40° C.) was transferred to a 4 L separatory funnel using rinses of 600 mL of nitrogen purged distilled water and 0.5296 kg (600 mL) of toluene. The two phases were mixed and then allowed to separate. A small quantity of solid at the interface was discarded. The aqueous layer was extracted consecutively with toluene (2×0.5196 kg, 2×600 mL) and heptane (0.5472 kg, 800 mL). The organic phases (Extract A) were discarded by the Waste Treatment procedure described below. A sufficient amount of nitrogen purged distilled water was added to the aqueous layer to achieve a volume of 3.60 L.

A 12 L multi-necked flask was equipped with a mechanical stirrer, a thermometer, and a condenser with a nitrogen inlet. The flask was purged with nitrogen and a nitrogen atmosphere was maintained in the flask.

The 3.60 L aqueous layer was transferred to the empty 12 L flask. The stirred solution was cooled under nitrogen to 10–15° C. with an ice/water bath. From a 1000 mL pressure equalizing dropping funnel, 410 mL of 12 N hydrochloric acid was added dropwise to the stirred solution while maintaining the temperature at 10–15° C. with the ice/water bath and until a pH of 3.5±0.2 was reached. A small precipitate was formed.

The resulting suspension was filtered through a Celite pad on polypropylene cloth in a 19 cm Buchner funnel into a 5 L multi-necked flask equipped with a mechanical stirrer, a thermometer, a condenser with a nitrogen inlet and a 1000 mL pressure equalizing dropping funnel. The filter pad was washed with 300 mL of nitrogen purged distilled water.

The filter funnel was removed. The system was flushed with nitrogen and again maintained in a nitrogen atmosphere. To the stirred solution, 76 mL of 10 N sodium hydroxide was added from the dropping funnel until a pH of 9.6±0.2 was reached. The resulting slurry of crystals was cooled to 5–10° C. and the slurry of crystals was maintained at 0–5° C. for about 1 hour.

The solid was collected on a polypropylene cloth in a 19 cm Buchner funnel. The filter cake was washed with 3×200 mL of nitrogen purged distilled water. The filtrate was discarded.

A 12 L multi-necked flask was equipped with a mechanical stirrer, a thermometer, and a condenser with a nitrogen inlet. The flask was purged with nitrogen and a nitrogen atmosphere was maintained in the flask. The flask was charged with 3000 mL of nitrogen purged distilled water and cooled to 15–20° C. with an ice/water bath. The solids collected on the polypropylene cloth were added to the stirred water in the flask and stirred at 15–20° C. until a smooth suspension was obtained (about 30 minutes).

The solid was collected on a polypropylene cloth in a 19 cm Buchner funnel using 600 mL of nitrogen purged distilled water to complete the transfer. The filter cake was washed with water (3×300 mL) and filtered. A dam was formed on top of the filter with a sheet of latex rubber and an aspirator vacuum was applied to the filter flask for about 5 hours. The white solid was dried in a vacuum oven under oil pump vacuum at 80° C. for about 18 hours. The solid was crushed and re-dried if necessary to constant weight. The yield was 90.7% (172.3 g) (HPLC Analysis: Strength or Purity (w/w): 98.8%, Impurities (excluding inorganics) (w/w): 0.046%, Ash (inorganics) (w/w): 0.14%).

Waste Treatment

The waste to be discarded contained byproducts, such as tris(1-methylpropyl)-borane and tris(1-methylpropyl)-boroxin. A 22 L or 50 L multi-necked flask was equipped with a mechanical stirrer, a thermometer, and a condenser with a nitrogen inlet. The flask was purged with nitrogen using a Firestone valve and a nitrogen atmosphere was maintained in the flask.

Distillate A and Extract A were combined in the flask to obtain a biphasic mixture (4.00 L with 400 mL of an aqueous bottom phase) under a nitrogen atmosphere. The stirrer was started and 600 mL of 10 N sodium hydroxide and 600 mL of water were added. A slurry of sodium perborate tetrahydrate (1.848 kg, 12.01 moles, ~3 equivalents per mole of tris(1-methylpropyl)borane) in 12 L of water was added in portions with ice/water cooling over about 20 minutes to maintain the temperature at 28–38° C. After the exotherm had subsided, the mixture was stirred at 22–23° C. under a nitrogen atmosphere for about 18 hours. The solid dissolved and two liquid phases remained.

The stirrer was stopped and the phases were allowed to separate. The upper phase was examined by gas chromatography/mass spectrometry to determine if any tris(1-methylpropyl)borane or tris(1-methylpropyl)boroxin was still detectable. If any was detected, 80 g (0.52 mol) of sodium perborate was added as a slurry in 400 mL of water and the solution was stirred at 22–23° C. for about 18 hours. Once tris(1-methylpropyl)borane and tris(1-methylpropyl)boroxin were no longer detectable in the upper phase, the aqueous phase was checked for its oxidizing capability (for example, due to peroxides and excess sodium perborate) with starch iodide paper.

The phases of the solution were then separated. The top organic layer was combined with other organic waste from the synthesis to be discarded. The aqueous layer was combined with other aqueous waste from the synthesis to be discarded.

The following procedures were used in the Examples 7–11 below.

X-Ray Powder Diffraction

XRPD analyses were carried out on a Shimadzu XRD-6000 X-ray powder diffractometer using Cu Kα radiation. The instrument is equipped with a fine focus X-ray tube. The tube power and amperage were set at 40 kV and 40 mA, respectively. The divergence and scattering slits were at 1° and the receiving slit was set at 0.15 mm. Diffracted radiation was detected by a NaI scintillation detector. A theta-two theta continuous scan at 3°/min (0.4 s/0.02° step) from 2.5 to 40° 2θ was used. A silicon standard was analyzed each day to check the instrument alignment.

In cases where preferred orientation [vide infra] occurred during X-ray powder diffraction, the ODV succinate was sometimes placed between folded weighing paper, then ground with an agate pestle and re-analyzed by XRPD.

Thermogravimetric Analysis (TGA)

Figure 8:
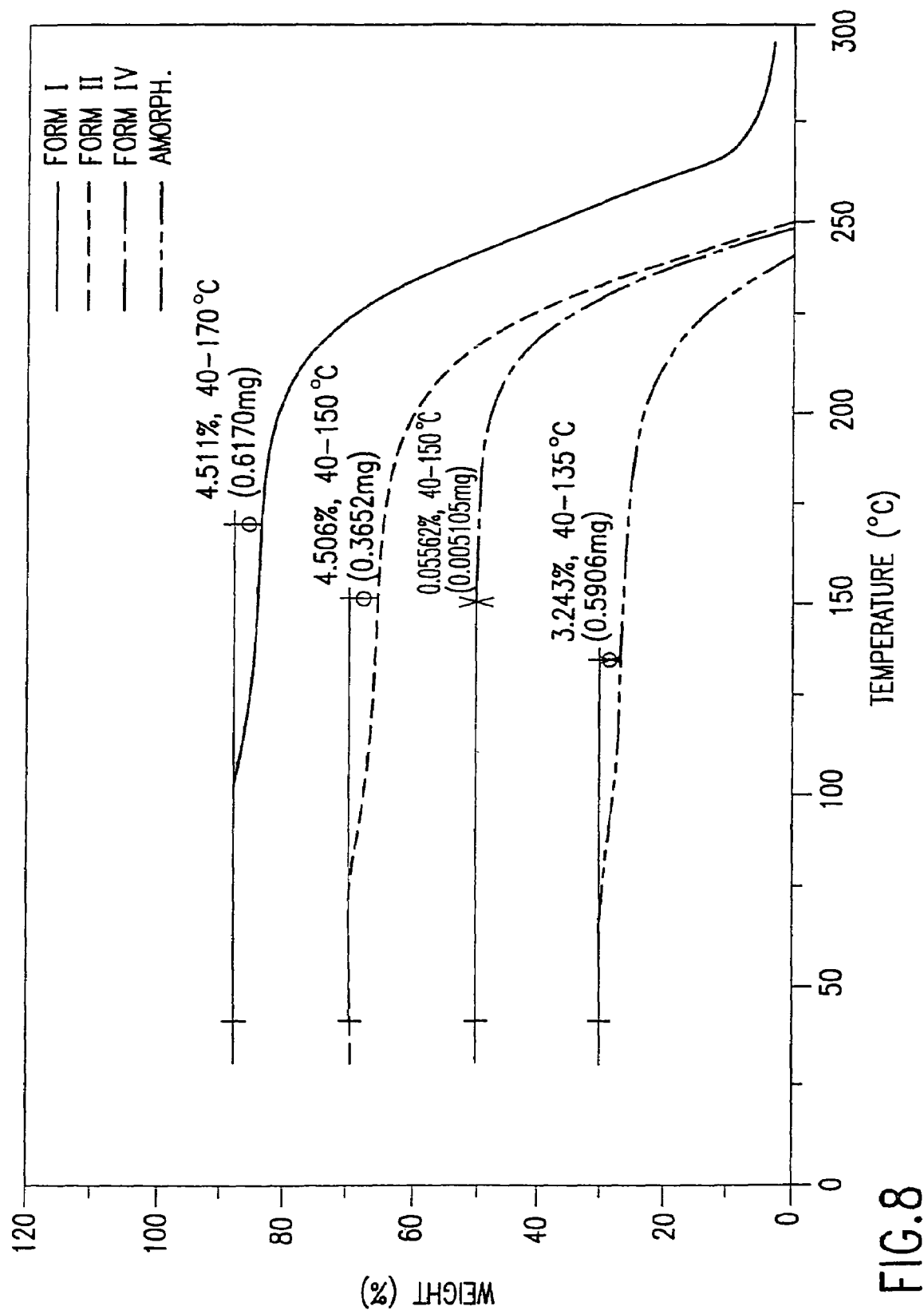
FIG. 8 are thermogravimetric analyses (TGA) of Forms I, II, and IV and the amorphous form of ODV succinate heated from 25 to 300° C. at a scan rate of 10° C./minute under a nitrogen purge.

Thermogravimetric analysis was conduct on a TA Instruments 2950 thermogravimetric analyzer. The calibration standards were nickel and Alumel™. Approximately 8–20 mg of sample were placed in the pan, accurately weighed, and inserted into the TG furnace. The samples were heated under nitrogen at a rate of 10° C./min, up to a final temperature of 300° C. Weight derivative (%/° C.) was used to determine total weight loss between 40° C. and the temperature at which the derivative was zero (usually 150° C.). The results of TGA for Examples 8–12 below are shown in FIG. 8.

Different Scanning Calorimetry

Figure 6:
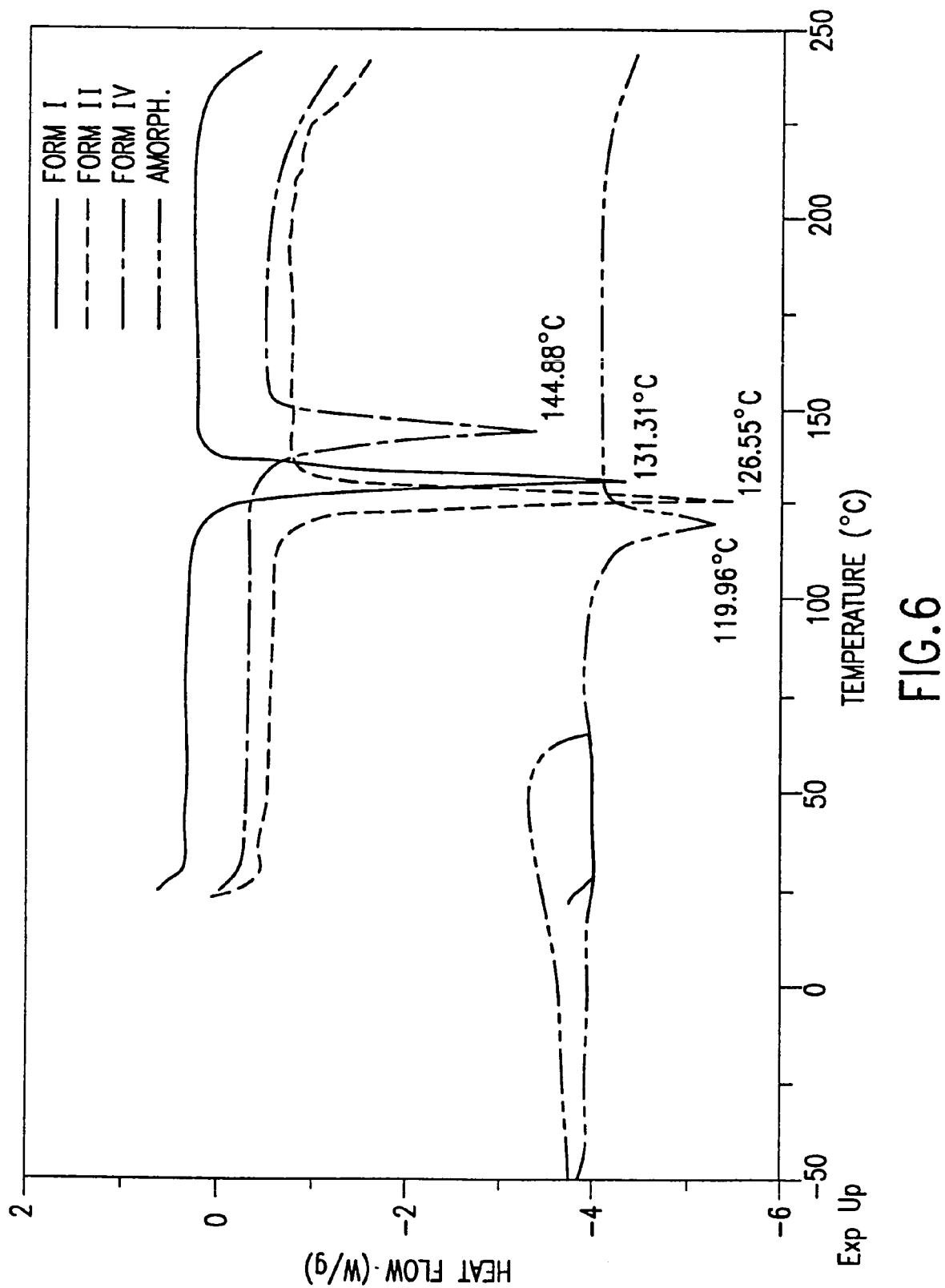
FIG. 6 are differential scanning calorimetry (DSC) analyses of Forms I, II, and IV and the amorphous form of ODV succinate from 25 to 250° C. in hermetically-sealed pans at a scan rate of 10° C./minute under a nitrogen purge.

DSC analyses were carried out on a TA Instruments differential scanning calorimeter 2920. Approximately 3–5 mg of sample was placed into a DSC pan, and the weight accurately recorded. The pan was hermetically sealed. Each sample was heated under nitrogen at a rate of 10° C./min, up to final temperature of 250° C. Indium metal was used as the calibration standard. Reported DSC temperatures are at the transition maxima. The results of DSC for Examples 8, 9, 11, and 12 below are shown in FIG. 6.

DSC Glass Transition

For studies of the glass transition temperature ($T_g$) of the amorphous material, the sample was heated under nitrogen at a rate of 10° C./min up to a final temperature of 250° C. The sample pan was hermetically sealed.

EXAMPLE 7

Preparation of Form I of ODV Succinate

A 5 L multi-necked flask, equipped with a stirrer, a thermometer, and a condenser, with a nitrogen inlet attached to a Firestone valve were placed in a heating mantle. The system was purged with nitrogen and a nitrogen atmosphere was maintained. 1.668 kg (2111 mL) acetone and 0.667 kg (667 mL) water were charged into the flask. The stirrer was started and 0.250 kg (0.949 mol) O-desmethyl-venlafaxine free base (prepared as described in Example 6) were added. The suspension was stirred for 30 minutes. 0.1155 kg (0.978 mol) succinic acid were added and the transfer was completed with rinses of acetone (0.186 kg, 236 mL) and water (0.075 kg, 75 mL). The suspension was stirred, warmed to 60° C. (±3° C.), and maintained at 60° C. (±3° C.) while being stirred for 30–60 minutes. A clear to cloudy solution was obtained. The mixture was then filtered through a filter comprised of polypropylene cloth with a filter paper underlay into a 5 L multi-necked flask equipped with a mechanical stirrer, a thermometer, and a condenser fitted with a vacuum outlet. The filter funnel was rinsed with warm (50–60° C.) aqueous acetone (24:76 v/v, 427 mL). The system was purged with nitrogen and the solution was cooled to 30–35° C. to induce crystallization. The stirred slurry of crystals was maintained at that temperature for about 4 hours. The stirred slurry of crystals was cooled to 0–5° C. and maintained at that temperature for about 1 hour. The crystals were collected on a polypropylene cloth filter with a filter paper underlay in a 15 cm funnel. The filter cake was washed with cold (0–5° C.) aqueous acetone (24:76 v/v, 2×300 mL) and filtered for 5 minutes. A dam was formed on top of the filter with a sheet of latex rubber. An aspirator was applied to the filter cake for 1 hour. The weight of the filter cake was about 0.351 kg. The product was dried under vacuum (50 mm Hg) at 30±5° C. for 12 hours. The product was then dried under vacuum (50 mm Hg) at 45×5C. for 24 hours.

An XRPD of the ODV succinate is shown in FIG. 1.

Alternative Preparation of Form I of ODV Succinate

A 5 L multi-necked flask equipped with a stirrer, a thermometer, and a condenser with a nitrogen inlet attached to a Firestone valve are placed in a heating mantle. The system is purged with nitrogen and a nitrogen atmosphere was maintained. 1.651 kg (2090 mL) acetone and 0.660 kg (660 mL) water are charged into the flask. The stirrer is started and 0.250 kg (0.949 mol) O-desmethyl-venlafaxine free base (prepared as described in Example 6) are added. The suspension is stirred for 30 minutes. 0.1155 kg (0.978 mol) succinic acid are added. The suspension is stirred, warmed to 60° C. (±3° C.), and maintained at 60° C. (±3° C.) while being stirred for 30–60 minutes. The mixture is then filtered through a filter comprised of Celite on polypropylene cloth with a filter paper underlay into a 5 L multi-necked flask equipped with a mechanical stirrer, a thermometer, and a condenser fitted with a vacuum outlet. The filter funnel is rinsed with warm (50–60° C.) aqueous acetone (24:76 v/v, 427 mL). The system is purged with nitrogen and the solution is cooled to 30–35° C. to induce crystallization. The stirred slurry of crystals is maintained at that temperature for about 4 hours. The stirred slurry of crystals is cooled to 0–5° C. and maintained at that temperature for about 1 hour. The crystals are collected on a polypropylene cloth filter with a filter paper underlay in a 15 cm funnel. The filter cake is washed with cold (0–5° C.) aqueous acetone (24:76 v/v, 2×300 mL) and filtered. A dam for the filter cake is formed with a sheet of latex rubber. An aspirator is applied to the filter cake for 1 hour. The weight of the wet cake is about 0.351 kg. The product is dried under vacuum (50 mm Hg) at 30±5° C. for 12 hours. The product is then dried under vacuum (50 mm Hg) at 45±5° C. for 24 hours. The yield was 85.8% (325.2 g) (HPLC Analysis: Impurities (excluding inorganics) (w/w): 0.0%, Ash (inorganics) (w/w): 0.0%, Amount of any single impurity (w/w): <0.01%).

EXAMPLE 8

Preparation of Form II of ODV Succinate

Form II was prepared by dissolving 306.1 mg of Form I in 200 ml acetone, filtering the solution through a 0.2 um nylon disc followed by vacuum stripping the filtrate on a rotary evaporator at ambient temperature.

An XRPD of the ODV succinate is shown in FIG. 2.

EXAMPLE 9

Preparation of Form III of ODV Succinate

Form III was prepared using two different milling techniques. In the first technique, ball-mill grinding, 290.2 mg of Form I was measured into a stainless steel cylinder with a ball, the sealed container was placed on a Retsch Mixer and milled for five minutes at a frequency of 30/s. At the end of the cycle, a spatula was used to scrape material from the walls. The procedure was repeated three times for a total mill time of 20 minutes. In the second technique, cryo-grinding, 40.5 mg of Form I was charged to a stainless steel cylinder with a rod, the sealed container was then placed in a SPEX Freezer mill maintained at −96 degrees Celsius with liquid nitrogen. The material was milled for two minutes at a frequency of 10/s (20 impacts per second), then cooled for two minutes. The procedure was repeated two times for total mill time of six minutes.

An XRPD of the ODV succinate is shown in FIG. 3.

EXAMPLE 10

Preparation of Form IV of ODV Succinate

Form IV was prepared in the following manner: A mixture of equal amounts of Form I and Form II was charged to a saturated, 0.2 um-filtered solution of acetonitrile-ODV succinate at 54 degrees Celsius. The mixture was agitated for a period of eight days. The slurry was filtered and the recovered solids air-dried. The solids were then charged to a 2-dram scintillating vial and heated for eighteen hours at 120° C.

An XRPD of the ODV succinate is shown in FIG. 4.

EXAMPLE 11

Preparation of Amorphous Form of ODV Succinate

The amorphous form of ODV succinate was prepared by charging a mixture of 854.1 mg of Forms I and II to an open, 20-ml scintillating vial and then placing the vial in a 150° C. oil bath for about 18 minutes.

An XRPD of the ODV succinate is shown in FIG. 5. According to DSC, the $T_g$ onset occurs at 18° C.

EXAMPLE 12

Preparation of Form II of ODV Succinate 56 g of O-desmethyl-venlafaxine, 26 g of succinic acid, 112 g of acetone, and 112 g of purified water were charged into a container. The resulting slurry was heated to reflux (about 62° C.) until a solution formed. The solution was cooled slightly and 1.2 g of charcoal 2S was charged. The solution was refluxed for about 15 minutes. The solution was filtered through a Seitz filter and the filter cake was washed with 5 g of acetone. The hot solution was then charged into a bulb equipped with a reflux condenser. A vacuum was applied from the top of the condenser. The solution began to boil and crystallize. The solution was stirred. The vacuum was applied until the slurry reached 20° C. The solution was cooled with an external ice bath to 5° C. The crystals were isolated by suction filtration. The filter cake was washed with a mixture of 11 g of purified water and 45 g of acetone. Air was sucked through the cake for about 2 hours. About 70 g of ODV succinate was formed.

Alternative Preparation of Form II of ODV Succinate by Fast Crystallization

A 2 L 4-neck flask was charged with O-desmethyl-venlafaxine (75.0 g, 0.285 mol), acetone (627 mL), succinic acid (34.50 g, 0.29 mol), and water (197.5 mL). The suspension was warmed to 60° C. and filtered through a pad of Celite. The filter pad was washed with a warm mixture of acetone (97 mL) and water (30.6 mL). The filtrate was transferred to a clean 2 L flask rinsing with acetone (50 mL). The temperature of the solution was 28° C. The solution was allowed to cool and crystallization began at 23° C. The mixture was then rapidly cooled in an ice/water bath to 0–5° C. The mixture was stirred at 0–5° C. for 2 hours. The solids were isolated by filtration and washed with cold aqueous acetone (2×200 mL, 25:75 v/v water/acetone). The wet filter cake was dried in a vacuum oven at 35±5° C. (50 mm Hg) for 48 hours to yield ODV succinate monohydrate as white crystals (89.5 g, 78.7%).

$^1$H NMR (300 MHz, DMSO-$d_6$) 10–9 (bs, 2H), 7.00 (d, J=8.2 Hz, 2H), 6.65 (d, J=8.2 Hz, 2H), 3.4–3.2 (bs, 1H), 3.12 (dd, J=7.0, 12.2 Hz, 1H), 2.74 (t, J=8.7 Hz, 1H), 2.7–2.58 (m, 1H), 2.50 (s, 3H), 2.36 (s, 3H), 2.28 (s, 4H), 1.50–1.25 (m, 6H), 1.20–0.80 (4H).

EXAMPLE 13

Rat Jejuvanal Test

The rat intestine perfusion technique is a direct way to measure the regional absorption properties of a test compound in the gastrointestinal tract. Rat intestinal permeability coefficient (Peff) can be used to predict human in vivo oral absorption of passively absorbed compounds. Fagerholm, M. Johansson, and H. Lennernäs, "Comparison between permeability coefficients in rat and human jejunum", *Pharm. Res.*, 13, 1996, 1336–1342, have demonstrated a good correlation between rat Peff and human fraction of dose absorbed (Fa) for a series of compounds. Meanwhile, some other characteristics such as formulable Maximum Absorbable Dose (MAD), FDA Biopharmaceutical Classification, etc. can also be estimated.

Materials

Perfusion buffer (PB) consisted of KCl (5.4 mM), NaCl (48 mM), $Na_2HPO_4$ (28 mM), $NaH_2PO_4$ (43 mM), mannitol (35 mM), polyethylene glycol (PEG)-4000 (0.1%, w/v), glucose (10 mM). The pH was adjusted to 6.8 with NaOH and osmolarity was adjusted to 290+10 mOsm/l with 1.0 M NaCl. Before the experiment, $^{14}$C-PEC-4000 (0.02 µCi/mL), 3H-mannitol (0.025 µCi/mL), metoprolol (20 µg/mL), and ODV succinate or fumarate (50 µg/mL) were added.

Rats used in this study were Charles River CD males, ranging in weight from approximately 300–350 grams.

Internal Standard Compounds

Metoprolol (a well-absorbed and passively transported compound) was used as a standard and tested simultaneously along with the ODV compounds. Glucose (a well-absorbed and actively transported compound) was used to monitor the physiological functionality of the intestinal barriers. $^{14}$C-labeled PEG-4000 was used as a non-absorbable marker to describe the water flux across the intestinal wall. $^3$H-labeled mannitol was used as a paracellularly transported marker to indicate the integrity of the intestinal tight junctions.

Analytical Methods

All chemicals were of analytical grade. After each experiment, all the analytic assays were performed promptly. For isotope determinations, 0.5 mL of perfusate sample containing $^{14}$C PEG-4000 and $^3$H-mannitol was mixed with 5 mL of scintillation cocktail. Radioactivity was counted in a liquid scintillation counter (Wallac 1409). Glucose concentration was determined by the glucose oxidase method (Biochemistry Analyzer). Metoprolol and the ODV compounds were analyzed by HPLC-UV/Vis (HP-1100 with a diode-array detector), using a YMC AQ 120µ, 5µ, 150×4.6 mm column and step gradient mobile phase containing water/0.1% TFA and acetonitrile. The ODV compounds and metoroplol were detected at 226 and 272 nm UV wavelength, respectively. Blank perfusate was assayed to evaluate the interference at these chromatographic conditions.

In Situ Rat Jejunal Perfusion

The perfusions were performed in three intestinal sections of anesthetized rats: duodenum-jejunum, ileum, and colon. The lengths of the segments were approximately 10–12 cm for small intestine segments and 5–6 cm for colon segments. An inflow cannula was inserted at the proximal end and an outflow cannula was inserted at the distal end. Perfusate was pumped through the segment at 0.19 mL/min, and collected at 20, 40, 55, 70, 85 and 100 minutes.

ODV succinate or fumarate was added to the perfusion working buffer at a concentration of 50 µg/mL, which is approximately equivalent to a 200 mg human does. The disappearance rates of ODV compound, metoprolol, and glucose were determined from each collection interval by comparing to the initial compound solution remaining in the syringe at the end of the 100 minutes. This is to correct for any losses due to binding to the syringe or tubing. Meanwhile, drug concentration in perfusate samples were corrected for water influx/efflux, which was computed, based on $^{14}$C-PEG-4000 concentration changes.

Data Analysis a. Recovery and Water Flux

Recovery of $^{14}$C-PEG-4000 was determined to provide information on the integrity of the perfused intestinal segment:

$$\% \ PEG_{rec} = (\Sigma PEG_{out}/\Sigma PEG_{in})*100$$

Overall $^{14}$C-PEG-4000 recovery was calculated and any data for which the individual recovery fell outside of the range of 96%–103% was excluded from the data set. Values below this range would indicate tissue damage that allows passage of PEG-4000 outside of the perfused segment, while values above this range would indicate significant water movement out of the segment.

Water movement across the gut wall was determined by calculation of net water fluid:

$$\text{Net Water Flux } (NWF) = [(1 - PEG_{out}/PEG_{in})*Q]/L$$

where $PEG_{out}$ and $PEG_{in}$ are the amount of radioactivity (dpm) of $^{14}$C-PEG-4000 in inlet and outlet sides of the perfused intestinal segment, respectively; Q is the flow rate of perfusate; and L is the length of perfused segment (cm).

b. Peff Calculation

The presence of the ODV compound in the perfusate was determined by HPLC. The amount of drug present at each time point was corrected for water movement across the wall of the intestine:

$$C_{out,corr} = C_{out}*(PEG_{in}/PEG_{out})$$

where $C_{out}$ is the concentration of drug in outlet perfusate; $C_{out,corr}$ is the concentration of drug in outlet perfusate corrected for water moving in or out of the segment, as determined by the recovery of $^{14}$C-PEG-4000.

Effective intestinal permeability, Peff (cm/sec), was determined by the following equation:

$$Peff = [Q*(C_{in}-C_{out,corr})/C_{in}]/2\ \mu rL$$

where Q is the flow rate; $C_{in}$ is the concentration of drug in inlet perfusate; $2\ \mu rL$ is the inner surface area of the perfused segment, with r assumed to be 0.18 cm in the rat (see G. Amidon, H. Lennernäs, V. Shah, J. Crison. "A theoretical basis for a biopharmaceutic drug classification: The correlation of in vitro drug product dissolution and in vivo bioavailability." *Pharm. Res.* 12, 1995, 413–420) and L the length of the perfused segment (cm).

c. Fraction Absorbed (Fa)

The fraction of dose absorbed, Fa, in human is currently predicted from (Fagerholm, M. ibid:

$$Fa = 100*(1 - e^{-(2*(\alpha*Peff,rat+\beta)*(tres/r))})$$

where α and β are the correction factors, tres is the residence time in human small intestine; and r is the radius of the human small intestine.

d. Maximum Absorbable Dose (MAD)

The maximum absorbable dose, MAD, in humans can be calculated as:

$$MAD = ka * \int_0^t Cs * V * dt$$

$$MAD = ka * Cs * V_0 * tres$$
$$= (2*Peff, h/r) * Cs * V_0 * tres$$

where ka is a first-order absorption rate constant; tres is the residence time in a human small intestine; r is the radius of the human small intestine, and $V_o$ is the estimated volume of fluid present in the gastrointestinal tract. See Johnson, K. C., Swindell, A. C. "Guidance in setting of drug particle size specifications to minimize variability in absorption". *Pharm. Res.* 13(2), 1996, 1795–1798).

Results

Stability in Jejunal Fluids

The stability of ODV succinate or fumarate in the solutions of blank perfusion buffer (Pβ), and jejunal fluids (perfusion buffer collected by washing the isolated jejunal segment, pH=6.8) was determined at 37° C. for up to 6 hours. The results indicated than no apparent degradation/metabolism of these two salt forms was evident under these test conditions. The results for ODV Succinate are presented in Table 7 below. Similar data was obtained for ODV fumarate.

TABLE 7

| Incubation Time (hours) | Blank Perfusion Buffer[1] (ODV Succinate) | Intestinal fluid[1,2] (ODV Succinate) |
|---|---|---|
| 0 | 100.0 | 100.0 |
| 2 | 99.9 | 99.6 |
| 3 | 100.3 | 99.8 |
| 6 | 99.9 | 100.1 |

[1]The data is the relative percentage remaining (%) of HPLC peak area at different time points over time zero.
[2]Total protein concentration approximately 0.2 mg/ml.

Rat Jejunal Perfusion Results

Site-Specific Absorption of ODV Succinate

The Peff values for ODV succinate in the small intestine ($0.912\pm0.067\times10^{-5}$ cm/sec in duodenum-jejunum, $1.73\pm0.22*10^{-5}$ cm/sec in ileum) were lower than metoprolol's Peff values. The Peff value of ODV succinate in the colon was found to be $0.062\pm0.031\times10^{-5}$ cm/sec, which is about 10% of metoprolol's Peff value in the colon. The ileum segment seems to be the best absorption site for ODV succinate. The Peff's ratio of duodenum-jejunum vs. ileum vs. colon was found to be 1.00:1.90:0.07, indicating that small intestinal sites of duodenum, jejunum, and ilcum predominate the oral absorption of this compound (μ90%) for an IR dosage form. (Dongzhou Liu, S. Ng, R. Saunders, "Effect of Polysorbate 80 on Transport of Mannitol, Glucose, and Water Flux in Rat Small Intestine", *PharmSci.*, 2, 2000; Doungzhou Liu, S. Ng, R. Saunders. "Investigating Intestinal Uptake of Zaleplon in site and Simulating/Predicting Oral Absorption in vivo", Submitted to *PharmSci.* 3(4), 2001).

Figure 9:
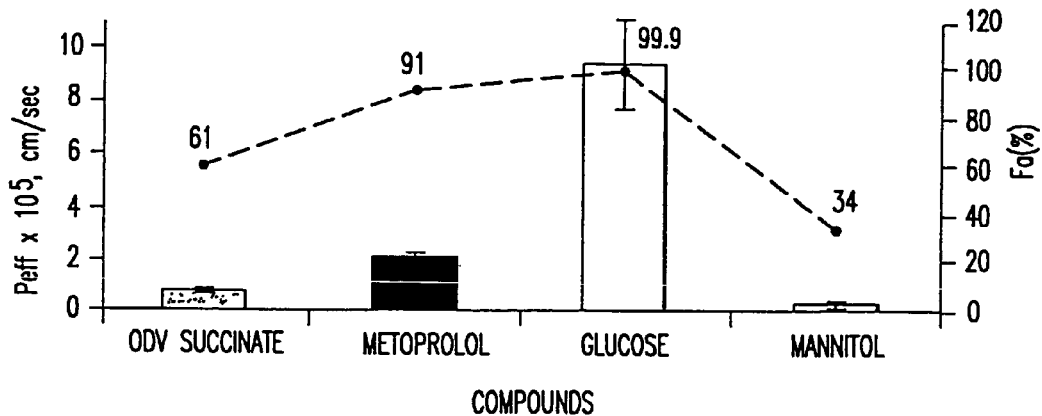
FIG. 9 is a graph of the rat intestinal permeability coefficient (Peff) experimentally determined in Example 14 and predicted human in vivo fraction of dose absorbed (Fa (%)) for ODV succinate, metoprolol, glucose, and mannitol.
Figure 10:
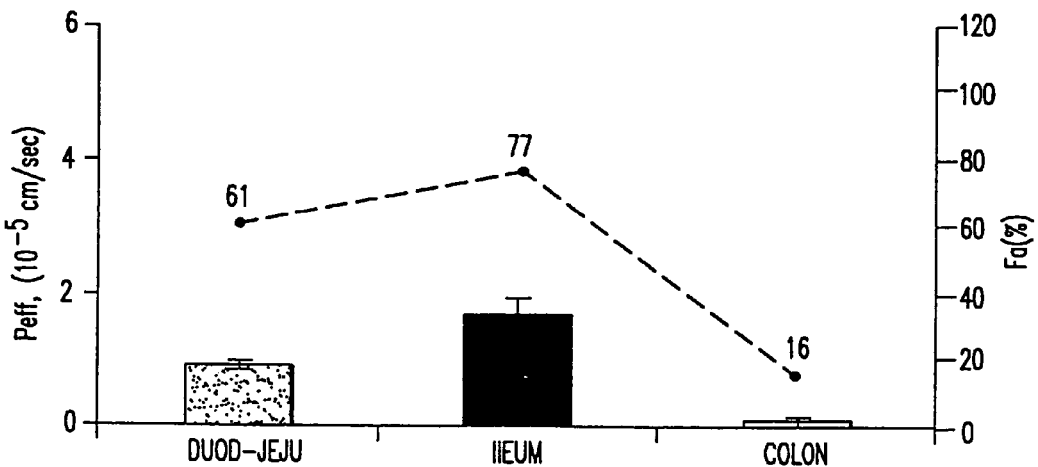
FIG. 10 is a graph of the Peff experimentally determined and Fa calculated in Example 14 for ODV succinate absorbed in the duodenum-jejunum, ileum, and colon.

Based on this experimental Peff, the human in vivo Fa of ODV succinate was predicted to be in the range of 60–77% in the small intestine and a Fa of 20% in the colon, as shown in FIGS. 9 and 10 and Table 8 below. The delivery vehicle was perfusion buffer (pH=6.8). The test at each absorption site was repeated with 3 rats and the Peff values were averaged.

TABLE 8

Rat Perfusion Data of ODV Succinate (50 μg/ml)

| Absorption Site | $Peff_{ODV\ Succinate}$ ($10^{-5}$ cm/sec) | $Peff_{Meloprolol}$ ($10^{-5}$ cm/sec) | $Peff_{ODV\ Succinate}/Peff_{Meloprolol}$ | Fa (%) (predicted human in vivo) |
|---|---|---|---|---|
| Jejunum | 0.912 ± 0.067 | 2.50 ± 0.11 | 0.37 ± 0.04 | 61.3 ± 2.5 |
| Ileum | 1.73 ± 0.22 | 3.22 ± 0.07 | 0.54 ± 0.07 | 76.6 ± 3.8 |
| Colon | 0.062 ± 0.031 | 0.583 ± 0.087 | 0.12 ± 0.07 | 16.4 ± 3.4 |

An estimated maximum absorbable dose (MAD) was generated based on the rat data. The MAD of ODV succinate in the entire gastrointestinal (GI) tract (human) was estimated to be about 8.6 grams, which is the sum of 2236 mg in the duodenum-jejunum, 5629 mg in the ileum, and 683 mg in the colon.

Site-Specific Absorption of ODV Fumarate

Figure 11:
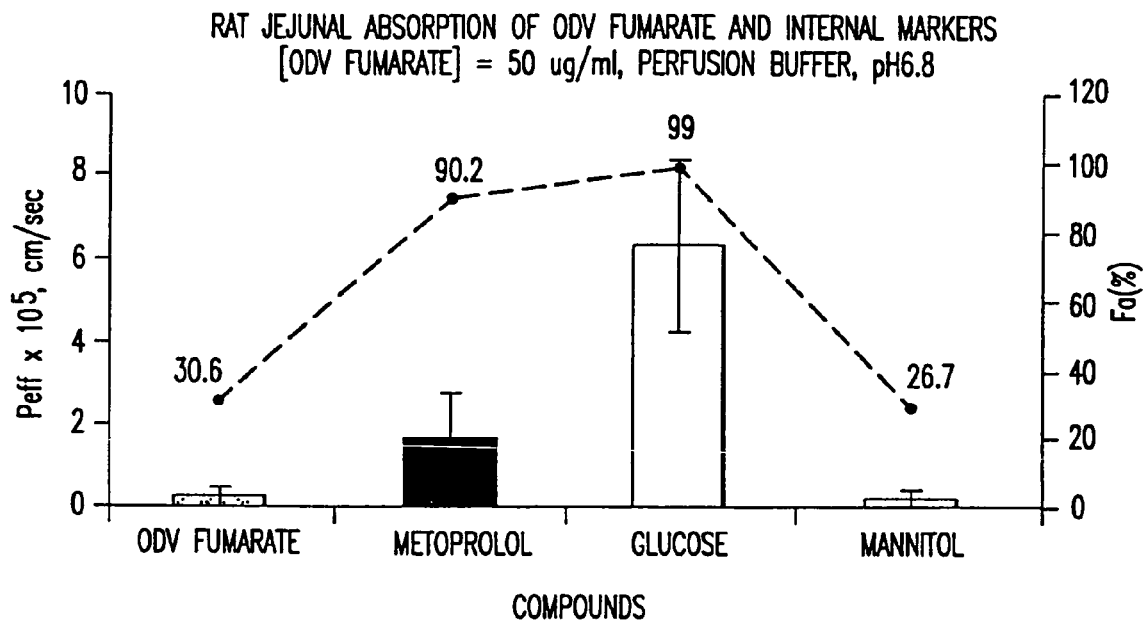
FIG. 11 is a graph of Peff experimentally determined and Fa calculated in Example 14 for ODV fumarate, metoprolol, glucose, and mannitol.
Figure 12:
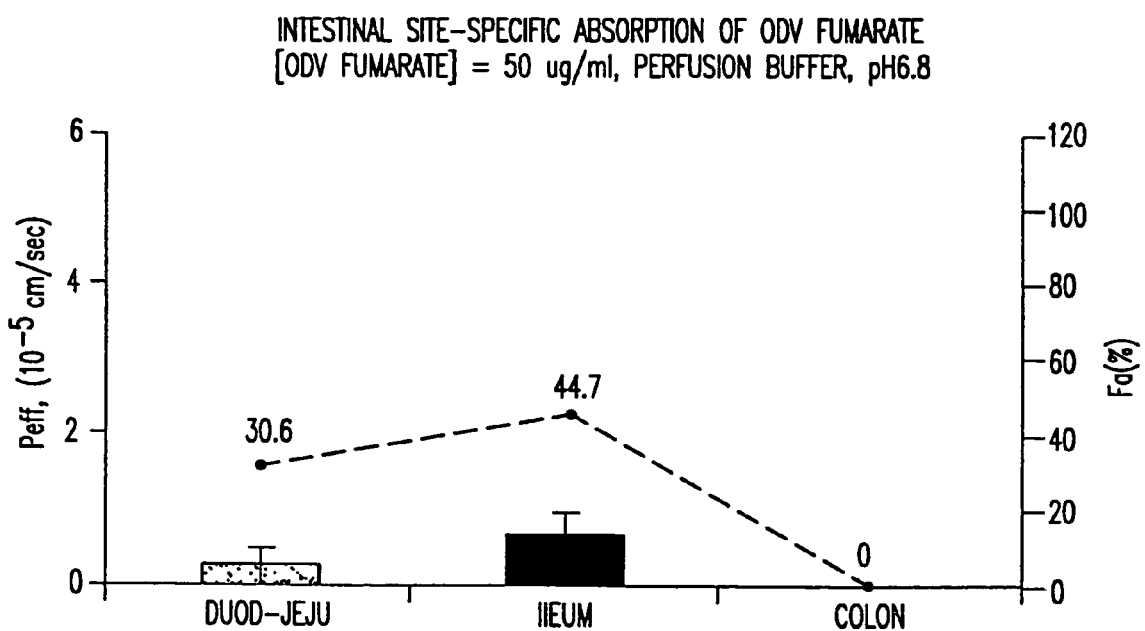
FIG. 12 is a graph of the Peff experimentally determined and Fa calculated in Example 14 for ODV fumarate absorbed in the duodenum-jejunum, ileum, and colon.
Figure 13:
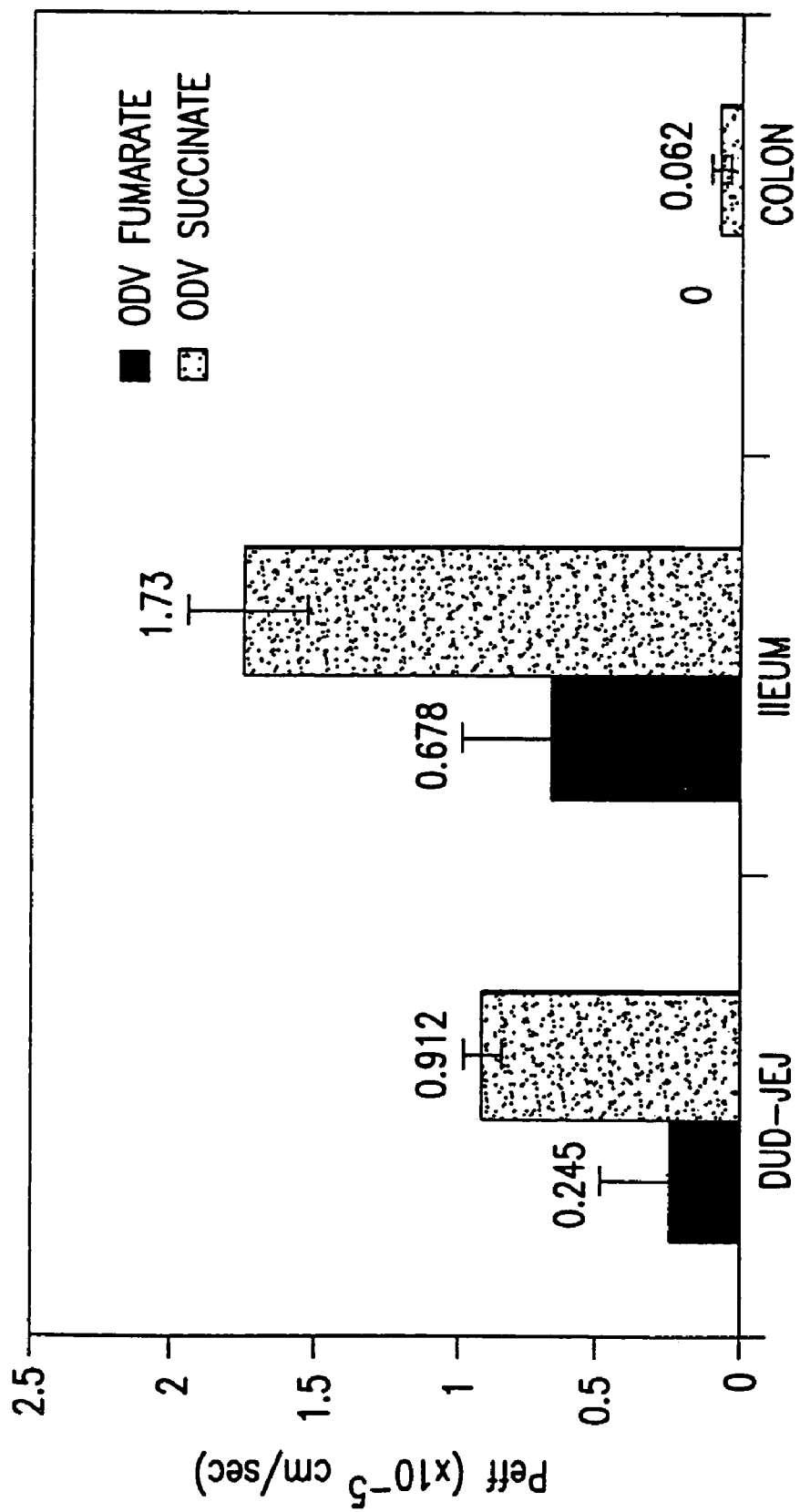
FIG. 13 is a comparison of the site specific absorption of ODV fumarate versus ODV succinate in the duodenum-jejunum, ileum, and colon in Example 14.

The site-specific absorption of ODV fumarate was investigated under the same study conditions as ODV succinate (50 μg/ml in pH 6.8 perfusion buffer). The test at each absorption site was repeated with 3 rats (except for in the Jejunum, where only 2 rats were tested) and the Peff values were averaged. The results are shown in Table 9 below and FIGS. 11, 12, and 13.

| Rat Perfusion Data of ODV Fumarate (50 ug/ml) | | | |
|---|---|---|---|
| Absorption Site | Peff$_{ODV\ Fumarate}$ ($10^{-5}$ cm/sec) | Peff$_{Meloprolol}$ ($10^{-5}$ cm/sec) | Peff$_{ODV\ Fumarate}$/ Peff$_{Meloprolol}$ | Fa (%) (predicted human in vivo) |
| Jejunum | 0.245 ± 0.237 | 1.78 ± 0.93 | 0.09 ± 0.08 | 30.6 ± 20.0 |
| Ileum | 0.678 ± 0.295 | 53 | 0.19 ± 0.06 | 44.7 ± 11.4 |
| Colon | 0 | 11 | 0 | 0 |

In general, the results show that ODV fumarate was less absorbed than ODV succinate in the rat GI tract. In the small intestine, the Peff values of the fumarate salt (0.24–0.68× $10^{-5}$ cm/sec) were only about 27µ40% of the succinate's Peff values. In the colon, no measurable absorption of ODV furmarate was found.

The in vivo Fa of ODV fumarate was estimated to be in the range of 33–45% in the small intestine and 0 in the colon, indicating an overall low absorption of this compound in the entire GI tract. The MAD was predicted to be about 440 mg.

The results of the site-specific intestinal absorption of ODV succinate and ODV fumarate show that ODV succinate has better absorption in the small intestine and in the colon than ODV fumarate. Several publications have demonstrated that there is high correlation between the rat perfusion model and in vivo human absorption (see e.g., Doungzhou Liu, S. Ng, R. Saunders. "Investigating Intestinal Uptake of Zaleplon in site and Simulating/Predicting Oral Absorption in vivo", Submitted to *PharmSci.* 3(4), 2001).

EXAMPLE 14

Bioavailability of O-desmethyl-venlafaxine in Beagle Dogs

Test Formulations

An intravenous solution containing 25 mg/mL of Form I of ODV succinate was prepared by mixing 3.8168 g (2.5% w/v) of the ODV succinate in a sufficient amount of water for injection, USP to obtain 100 mL of solution.

An oral solution containing 25 mg/mL of Form I of ODV succinate was prepared by mixing 3.8170 g (2.5% w/v) of the ODV succinate in a sufficient amount of water for injection, USP to obtain 100 mL of solution. Prior to administration, the oral solution (25 mg/mL) was diluted to a concentration of 7.5 mg/mL with water.

Tablets each containing the ingredients listed in the table below were prepared by the method described in Example 15 for preparing ODV Succinate Formulation #2.

| Ingredient | mg per tablet | % w/w |
|---|---|---|
| ODV Succinate (Form I was used in the preparation) | 116.70 (75.00 as free base) | 39.2 |
| HPMC 2208 USP 100, 100 SR | 175.05 | 58.8 |
| Magnesium Stearate | 5.95 | 2.0 |
| Purified Water USP | q.s. | q.s. |
| Total | 297.70 | 100.0 |

Capsules (HGC Size 0) each containing the ingredients listed in the table below were prepared by the method described in Example 15 for preparing ODV Succinate Formulation #1.

| Ingredient | mg per tablet | % w/w |
|---|---|---|
| ODV Succinate (Form I was used in the preparation) | 116.70 (75.00 as free base) | 39.5 |
| Microcrystalline Cellulose (Avicel PH200)* | 177.26 | 60.0 |
| Magnesium Stearate | 1.48 | 0.5 |
| Total | 295.44 | 100.0 |

*Available from FMC BioPolymer of Philadelphia, PA.

Study Animals

Six male beagle dogs with body weights ranging between 10.2 and 16.0 kg were used in this study. The dogs were housed and given free access to water and food.

Study Design

The six dogs were dosed in a 4 period study. In Period 1, the dogs received 1 mL of the intravenous solution. In Period 2, the dogs received 10 mL of the oral solution. In Period 3, the dogs received the tablet. In Period 4, the dogs received the capsule. There was a one week wash out period between the first two treatment periods and a one month wash out period between treatment periods 2 and 3. Between periods 3 and 4, there was a one week wash out period. For periods 1 and 2, all dogs were fasted overnight with free access to water and fed after the four-hour bleeding. For periods 3 and 4, all dogs were fed 30 minutes prior to dosing and with free access to water.

Blood Samples

In periods 1 and 2, blood samples were drawn from the jugular vein at 0 (predose), 0.05 (intravenous only) and 0.13 (intravenous only), 0.25, 0.5, 1, 1.5, 2, 3, 4, 8, 12, 24, 32, and 48 hours after dosing into 5 mL heparinized vacutainers and immediately placed on ice. In periods 3 and 4, blood samples were drawn from the jugular vein at 0 (predose), 0.25, 0.5, 1, 1.5, 2, 3, 4, 6, 8, 12, 16, 24, and 32 hours after dosing into 5 mL heparinized vacutainers and immediately placed on ice. Plasma was separated in a refrigerated centrifuge and stored at −70° C. Plasma samples were then assayed.

Sample Analysis

Plasma O-desmethyl-venlafaxine concentrations were determined by the HPLC method using mass spectrometric detection described in Hicks, D. R., Wolaniuk, D., Russel, A., Cavanaugh, N., Kraml, M., "A high-performance liquid chromatographic method for the simultaneous determination of venlafaxine and O-desmethylvenlafaxine in biological fluids", *Ther. Drug Monit.* 16:100–107 (1994), which is hereby incorporated by reference. Based on a 0.2 mL sample volume, the method has a limit of quantitation for O-desmethyl-venlafaxine of 5.05 ng/mL. Total O-desmethyl-venlafaxine levels were determined after incubating 0.2 mL of plasma samples in β-glucuronidase for ~18 hours. O-desmethyl-venlafaxine-glucuronide levels were determined by subtracting the O-desmethyl-venlafaxine (separate extraction procedure without the use of β-glucuronidase and analyzed by HPLC-MS) concentrations from the total O-desmethyl-venlafaxine concentrations.

Data Analysis

Noncompartmental pharmacokinetic parameters were calculated from the individual dog plasma O-desmethyl-venlafaxine and O-desmethyl-venlafaxine-glucuronide concentration-time profiles. Area under the plasma concentration-time curves ($AUC_{0-\mu}$) values were calculated by the addition of $AUC_{Last}$ ($AUC_{Last}$=the linear trapezoid rule from time zero to the last measurable plasma concentration, $CP_{Last}$) and $CP_{Last}$/lambda. The values for lambda were determined from the long-linear portion of the terminal slope of the plasma O-desmethyl-venlafaxine and O-desmethyl-venlafaxine-glucuronide concentration-time profile after the intravenous dose. The half-life ($t_{half}$) was calculated as $t_{half}$=0.693/lambda. The peak plasma concentration ($C_{max}$) and the time to reach $C_{max}$ ($t_{max}$) were noted directly from the plasma concentration-time profiles.

Absolute bioavailability was determined by comparing the dose normalized $AUC_{0-\mu}$ values following the intravenous administration.

Results

All levels reported as below limit of quantitation (BLQ) were assigned a value of zero for calculation purposes. The bioanalytical results demonstrated that O-desmethyl-venlafaxine-glucuronide levels account for the major portion of total circulating O-desmethyl-venlafaxine levels after the administration of ODV succinate.

Based on the total O-desmethyl-venlafaxine levels, the absorption of O-desmethyl-venlafaxine and ODV succinate is essentially complete from the oral formulation with 121%, 103% and 76% absolute bioavailability for the oral solution, capsule, and tablet formulations, respectively.

Mean (% CV) Bioavailability Parameters of ODV Succinate (Expressed as Free ODV Levels)

| | Oral Solution (75 mg) | Capsule (75 mg) | Tablet (75 mg) | Intravenous Solution (25 mg) |
|---|---|---|---|---|
| AUC (ng*hr/mL) | 835 (33) | 904 (29) | 677 (23) | 746 (14) |
| $C_{max}$ (ng/mL) | 450 (23) | 465 (37) | 115 (24) | — |
| $t_{max}$ (hr) | 0.50 (55) | 0.55 (68) | 2.92 (35) | — |
| Absolute Bioavailability (%) | 37 (25) | 40 (17) | 31 (24) | — |

Mean (% CV) Bioavailability Parameters of ODV Succinate in Beagle Dogs Expressed as ODV-glucuronide Levels

| | Oral Solution (75 mg) | Capsule (75 mg) | Tablet (75 mg) | Intravenous Solution (25 mg) |
|---|---|---|---|---|
| AUC (ng*hr/mL) | 17349 (14) | 13381 (14) | 11686 (18) | 4814 (11) |
| $C_{max}$ (ng/mL) | 3917 (33) | 2633 (20) | 1235 (15) | 856 (20) |
| $t_{max}$ (hr) | 2.50 (22) | 1.67 (24) | 3.67 (14) | 2.33 (22) |
| Absolute Bioavailability (%) | 121 (13) | 95 (9) | 81 (11) | — |

Mean (% CV) Bioavailability Parameters of ODV Succinate in Beagle Dogs (n = 6) Expressed as Total ODV Levels

| | Oral Solution (75 mg) | Capsule (75 mg) | Tablet (75 mg) | Intravenous Solution (25 mg) |
|---|---|---|---|---|
| AUC (ng*hr/mL) | 18184 (13) | 14285 (13) | 12362 (18) | 5560 (9) |
| $C_{max}$ (ng/mL) | 4026 (32) | 2841 (19) | 1337 (15) | N/A |

-continued

| Mean (% CV) Bioavailability Parameters of ODV Succinate in Beagle Dogs (n = 6) Expressed as Total ODV Levels | | | | |
|---|---|---|---|---|
| | Oral Solution (75 mg) | Capsule (75 mg) | Tablet (75 mg) | Intravenous Solution (25 mg) |
| $t_{max}$ (hr) | 2.5 (22) | 1.67 (24) | 3.67 (14) | N/A |
| Absolute Bioavailability (%) | 109 (13) | 86 (7) | 74 (12) | — |

EXAMPLE 15

18 human subjects were given 75 mg each of Effexor® XR (venlafaxine formulation) (available from Wyeth-Ayerst Pharmaceuticals of St. Davids, Pa.), ODV succinate formulation #1, and ODV succinate formulation #2 over three different periods.

ODV succinate formulation #1, which is a capsule, is shown in the table below.

| ODV Succinate Formulation #1 | | |
|---|---|---|
| Ingredient | mg per tablet | % w/w |
| ODV Succinate (Form I was used in the preparation) | 113.9 (75.00 as free base) | 33.5 |
| Lactose Fast Flow | 112.2 | 33.0 |
| Microcrystalline Cellulose (Avicel PH200)* | 112.2 | 33.0 |
| Magnesium Stearate | 1.7 | 0.5 |
| Purified Water | q.s. | q.s. |
| Total | 340.0 | 100.0 |

ODV succinate formulation #1 was prepared as follows. The ODV succinate was sieved through a 400 micron screen and dry mixed with lactose and microcrystalline cellulose in a high shear mixer. The resulting mixture was wet granulated in a high shear mixer with purified water and dried in an oven or fluid bed drier. The mixture was blended with magnesium stearate and encapsulated in a capsule (HGC Size 0).

ODV succinate formulation #2, which is a tablet, is shown in the table below.

| ODV Succinate Formulation #2 | | |
|---|---|---|
| Ingredient | mg per tablet | % w/w |
| ODV Succinate (Form I was used in the preparation) | 113.81 (75.00 as free base) | 37.94 |
| HPMC 2208 USP 100, 100 SR | 170.44 | 56.81 |
| Microcrystalline Cellulose (Avicel PH200)* | 7.50 | 2.50 |
| Talc | 6.75 | 2.25 |
| Magnesium Stearate | 1.50 | 0.50 |
| Purified Water | q.s. | q.s. |
| Total | 295.44 | 100.0 |

*Available from FMC BioPolymer of Philadelphia, PA.

ODV succinate formulation #2 was prepared as follows. The ODV succinate was sieved through a 400 micron screen and dry mixed with HPMC, microcrystalline cellulose, and talc in a high sheer mixer. The mixture was then wet granulated with purified water and dried in an oven or fluid bed drier. The resulting mixture was belnded with HPMC and talc. Magnesium stearate was added and the mixture was again blended. The mixture was then compressed into a tablet.

All doses were administered after subjects consumed a standardized medium-fat breakfast. Blood samples were taken 0.5, 1, 2, 4, 6, 8, 12, 16, 20, 24, 28, 36, 48, and 72 hours after administration. The plasma concentrations of venlefaxine and O-desmethyl-venlafaxine in each blood sample was determined by the method described in Hicks, D. R., Wolaniuk, D., Russel, A., Cavanaugh, N., Kraml, M., "A high-performance liquid chromatographic method for the simultaneous determination of venlafaxine and O-desmethylvenlafaxine in biological fluids", *Ther. Drug Monit.* 16:100–107 (1994), which is hereby incorporated by reference.

The results are shown in the table below.

| Plasma Concentrations of Venlafaxine* | | | | |
|---|---|---|---|---|
| Formulation | $C_{max}$ (ng/mL) | $t_{max}$ (hr) | $t_{1/2}$ (hr) | AUC (ng*hr/mL) |
| Effexor ® XR | | | | |
| Mean ± Stand. Dev. | 40 ± 16 | 5.9 ± 0.5 | 9.5 ± 2.4 | 628 ± 265 |
| % CV | 39.9% | 8.0% | 25.6% | 42.2% |
| Min–Max | 11–77 | 4–6 | 4.8–13.8 | 139–1292 |

Since ODV Succinate Formulations #1 and 2 do not include venlafaxine, the plasma concentrations of venlafaxine resulting from administration of them was zero.

Plasma Concentrations of O-desmethylvenlafaxine

| Formulation | $C_{max}$ (ng/mL) | $t_{max}$ (hr) | $t_{1/2}$ (hr) | AUC (ng*hr/mL) |
|---|---|---|---|---|
| Effexor ® XR | | | | |
| Mean ± Stand. Dev. | 88 ± 25 | 9.3 ± 2.9 | 13.2 ± 4.0 | 2430 ± 647 |
| % CV | 28.9% | 31.2% | 30.4% | 26.6% |
| Min–Max | 37–142 | 6–16 | 7.6–24.8 | 1582–3835 |
| ODV Succinate Formulation #1 | | | | |
| Mean ± Stand. Dev. | 282 ± 57 | 3.1 ± 1.3 | 9.4 ± 1.4 | 3491 ± 814 |
| % CV | 20.1% | 43.0% | 14.7% | 23.3% |
| Min–Max | 173–399 | 0.5–6 | 6.8–11.5 | 1667–5086 |
| ODV Succinate Formulation #2 | | | | |
| Mean ± Stand. Dev. | 135 ± 54 | 7.3 ± 5.5 | 9.3 ± 1.9 | 3185 ± 944 |
| % CV | 39.9% | 75.4% | 20.5% | 29.6% |
| Min–Max | 65–279 | 2–28 | 6.1–13.7 | 1100–4767 |

The table below shows the number of human subjects who experienced various adverse effects after administration of a singled dose of ODV Succinate Formulations #1 and 2.

Without being bound to any particular theory, it is believed that adverse effects observed with Formulation #1 are related to the peak blood plasma level and/or tmax of the formulation. By flattening the curve as in sustained release formulation, Formulation #2, the peak blood plasma level is reduced and the tmax delayed. Thus, in patients, as a flattened blood plasma concentration to time profile is achieved adverse event are reduced or eliminated. Thus, a pharmaceutical composition comprising a sustained release formulation of ODV succinate having a peak blood plasma profile of less than about 225 ng/ml will have reduced side effects such as nausea and emesis.

Adverse Effects After Administration of a Single Dose of ODV Succinate Formulations #1 and 2

| Adverse Effect | ODV Succinate Formulation #1 (n = 18) | ODV Succinate Formulation #2 (n = 18) |
|---|---|---|
| Nauseau (VAS > 5 mm) | 10 | 1 |
| Nauseau (VAS > 20 mm or spontaneous) | 6 | 1 |
| Vomiting | 2 | — |
| Diarrhea | 1 | — |
| Abdominal Pain | — | — |
| Headache | 2 | — |
| Vaso-vagal Malaise | 2 | — |
| Trismus | 1 | — |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties. To the extent that a conflict may exist between the specification and a reference, the language of the disclosure made herein controls.

What is claimed:

1. A method of preparing O-desmethyl-venlafaxine comprising the step of demethylating venlafaxine or a salt thereof with an alkali metal salt of a trialkyl borohydride.

2. The method of claim 1, wherein each alkyl group in the trialkyl borohydride is independently a $C_1$–$C_6$ alkyl.

3. The method of claim 2, wherein the alkali metal salt of a trialkyl borohydride is selected from L-selectride, K-selectride, lithium triethylborohydride, potassium triethylborohydride, and mixtures thereof.

4. The method of claim 3, wherein the alkali metal salt of a trialkyl borohydride is L-selectride.

5. The method of claim 1, wherein the demethylation step is performed at a temperature of from about 60 to about 140° C.

6. The method of claim 1, further comprising the step of converting the O-desmethyl-venlafaxine to O-desmethyl-venlafaxine succinate.

7. The method of claim 1, further comprising the step of deactivating any boron containing byproducts produced by the demethylation reaction.

8. The method of claim 7, wherein the deactivating step comprises oxidizing the boron containing byproducts.

9. The method of claim 8, wherein the oxidizing step comprises reacting the boron containing byproducts with an oxidizing agent selected from hydrogen peroxide, sodium perborate, and mixtures thereof.

10. The method of claim 8, wherein the oxidizing step comprises adding the boron containing byproducts to an oxidizing agent or a solution comprising an oxidizing agent.

11. A method of preparing O-desmethyl-venlafaxine comprising the steps of:
(a) demethylating venlafaxine or a salt thereof with an alkali metal salt of a trialkyl borohydride to yield an alkali metal salt of O-desmethyl-venlafaxine; and (b) converting the alkali metal salt of O-desmethyl-venlafaxine to the free base of O-desmethyl-venlafaxine.

12. The method of claim 11, wherein step (b) comprises neutralizing the alkali metal salt of O-desmethyl-venlafaxine with acid.

13. The method of claim 11, further comprising the step of (c) converting the free base of O-desmethyl-venlafaxine to O-desmethyl-venlafaxine succinate.

14. The method of claim 11, wherein the venlafaxine in step (a) is the free base of venlafaxine.

15. The method of claim 1 wherein the demethylation step is performed at about 90° C.

16. The method of claim 1 wherein the demethylation step is performed with 5.5 molar excess of trialkyl borohydride.

* * * * *